(12) United States Patent
Mayweg et al.

(10) Patent No.: US 7,563,910 B2
(45) Date of Patent: Jul. 21, 2009

(54) HETEROCYCLIC CANNABINOID RECEPTOR ANTAGONISTS

(75) Inventors: Alexander Mayweg, Loerrach (DE); Robert Narquizian, St. Louis (FR); Philippe Pflieger, Schwoben (FR); Stephan Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 413 days.

(21) Appl. No.: 11/125,382

(22) Filed: May 9, 2005

(65) Prior Publication Data
US 2005/0250769 A1  Nov. 10, 2005

(30) Foreign Application Priority Data
May 10, 2004  (EP)  .................. 04102005

(51) Int. Cl.
A61K 31/4025  (2006.01)
C07D 403/06  (2006.01)
C07D 405/06  (2006.01)

(52) U.S. Cl. ................. 548/517; 548/518; 514/422
(58) Field of Classification Search .......... 548/517, 548/518
See application file for complete search history.

(56) References Cited

U.S. PATENT DOCUMENTS

| | | | |
|---|---|---|---|
| 3,940,418 A | 2/1976 | Hamilton | |
| 5,462,960 A | 10/1995 | Barth et al. | |
| 5,596,106 A | 1/1997 | Cullinan et al. | |
| 5,624,941 A | 4/1997 | Barth et al. | |
| 6,355,631 B1 | 3/2002 | Achard et al. | |
| 6,479,479 B2 | 11/2002 | Achard et al. | |
| 6,518,264 B2 | 2/2003 | Achard et al. | |
| 6,566,356 B2 | 5/2003 | Achard et al. | |
| 6,734,176 B2 | 5/2004 | Achard et al. | |
| 6,858,603 B2 | 2/2005 | Achard et al. | |
| 6,872,717 B2 | 3/2005 | Achard et al. | |
| 2002/0019383 A1 | 2/2002 | Achard et al. | |
| 2002/0035102 A1 | 3/2002 | Achard et al. | |
| 2003/0055033 A1 | 3/2003 | Achard et al. | |
| 2003/0119810 A1 | 6/2003 | Achard et al. | |
| 2003/0162808 A1 | 8/2003 | Achard et al. | |
| 2004/0157823 A1 | 8/2004 | Achard et al. | |
| 2004/0235816 A1 | 11/2004 | Achard et al. | |
| 2005/0130953 A1 | 6/2005 | Achard et al. | |

FOREIGN PATENT DOCUMENTS

| | | |
|---|---|---|
| EP | 576357 | 3/1977 |
| EP | 656354 | 6/1997 |
| EP | 658546 | 5/2001 |
| EP | 2805810 A1 | 9/2001 |
| EP | 2805818 A1 | 9/2001 |
| FR | 2783246 A1 | 3/2000 |
| FR | 2805817 A1 | 9/2001 |
| WO | WO9602248 | 2/1996 |
| WO | WO9719063 | 5/1997 |
| WO | WO0015609 | 3/2000 |
| WO | WO0046209 | 8/2000 |
| WO | WO0132663 | 5/2001 |
| WO | WO 01/58869 | 8/2001 |
| WO | WO0164632 | 9/2001 |
| WO | WO0164633 | 9/2001 |
| WO | WO0164634 | 9/2001 |
| WO | WO0170700 | 9/2001 |
| WO | WO0228346 | 4/2002 |
| WO | WO03/007887 | 1/2003 |
| WO | WO 03027069 | 4/2003 |
| WO | WO 03027076 | 4/2003 |
| WO | WO 03040107 | 5/2003 |
| WO | WO 03/063781 | 8/2003 |

OTHER PUBLICATIONS

D.Shire, et al., J. Biol. Chem. 270 (8) (1995) 3726-31.
E. Ryberg, et al., FEBS Lett. 579 (2005) 259-264).
S. Munro, et. al., Nature 365 (1993) 61-65.
Y. Gaoni, et. al, J. Am. Chem. Soc., 86 (1964) 1646-1647.
R. Mechoulam (Ed.) in "Cannabinoids as therapeutic Agents", 1986, pp. 1-20, CRC Press.
R. G. Pertwee, Pharmaceut. Sci 3 (11) (1997) 539-545.
E. M. Williamson, F. J. Evans, Drugs 60 (6) (2000) 1303-1314.
R.G. Pertwee, Curr. Med. Chem., 6 (8) (1999) 635-664.
W.A. Devane, et al., Science 258 (1992) 1946-9.
V. Di Marzo, et al., Trends in Neuroscience 21 (12) (1998) 521-8.
A. C. Porter, C.C. Felder, Pharmacol. Ther., 90 (1) (2001) 45-60.
C.M. Williams, T.C. Kirkham, Psychopharmacology 143 (3) (1999) 315-317.
C. C. Felder, et al., Proc. Natl. Acad. Sci. U. S. A. 90(16) (1993) 7656-60.

(Continued)

*Primary Examiner*—Laura L. Stockton
(74) *Attorney, Agent, or Firm*—George W. Johnston; Dennis P. Tramaloni

(57) ABSTRACT

The present invention relates to compounds of formula I

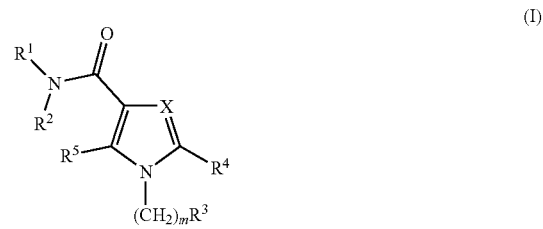

and pharmaceutically acceptable salts thereof. The compounds are useful for the treatment and/or prophylaxis of diseases which are associated with the modulation of CB1 receptors.

22 Claims, No Drawings

OTHER PUBLICATIONS

G. Colombo, et al., Life Sci. 63 (8) (1998) L113-PL117.

V. Di Marzo, et al., Nature 410 (6830) 822-825, Apr. 2001.

F. Barth, et al., "*Cannabinoid antagonists: From research tools to potential new drugs.*" Abstracts of Papers, 222nd ACS National Meeting, Chicago, IL, United States, Aug. 26-30, 2001, Abstract 294.

AAI; M. Pacheco, et al., J. Pharmacol. Exp. Ther. 257 (1) (1991) 170-183.

WIN54661; F. M. Casiano, et. al., NIDA Res. Monogr. 105 (1991) 295-6).

AM630, K. Hosohata, et al., Life Sci. 61 (1997) 115-118.

R. Pertwee, et al., Life Sci. 56 (23-24) (1995)1949-55.

LY320135, C. C. Felder, et al., J. Pharmacol. Exp. Ther. 284 (1) (1998) 291-7.

M. Kanyonyo, et al., Bioorg. Med. Chem. Lett. 9 (15) (1999) 2233-2236.

F. Ooms, et al., J. Med. Chem. 45 (9) (2002) 1748-1756.

HETEROCYCLIC CANNABINOID RECEPTOR ANTAGONISTS

BACKGROUND OF THE INVENTION

Two different subtypes of cannabinoid receptors ($CB_1$ and $CB_2$) have been isolated and both belong to G protein coupled receptor superfamily. Alternative spliced forms of $CB_1$, $CB_{1A}$ and $CB_{1B}$ have also been described, but are expressed only at low levels in the tissues tested. (D. Shire, C. Carrillon, M. Kaghad, B. Calandra, M. Rinaldi-Carmona, G. Le Fur, D. Caput, P. Ferrara, J. Biol. Chem. 270 (8) (1995) 3726-31; E. Ryberg, H. K. Vu, N. Larsson, T. Groblewski, S. Hjorth, T. Elebring, S. Sjögren, P. J. Greasley, FEBS Lett. 579 (2005) 259-264). The $CB_1$ receptor is mainly located in the brain and to a lesser extent in several peripheral organs, whereas the $CB_2$ receptor is predominately distributed in the periphery primarily localized in spleen and cells of the immune system (S. Munro, K. L. Thomas, M. Abu-Shaar, Nature 365 (1993) 61-61). Therefore in order to avoid side effects a $CB_1$-selective compound is desirable. $\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *cannabis sativa* (marijuanan), which is used in medicine since ages (R. Mechoulam (Ed.) in "*Cannabinoids as therapeutic Agents*", 1986, pp. 1-20, CRC Press). $\Delta^9$-THC is a non-selective $CB_{1/2}$ receptor agonist and is available in the USA as dronabinol (marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539-545, E. M. Williamson, F. J. Evans, Drugs 60 (6) (2000) 1303-1314).

Anandamide (arachidonylethanolamide) was identified as the endogenous ligand (agonist) for $CB_1$ (R. G. Pertwee, Curr. Med. Chem., 6 (8) (1999) 635-664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946-9). Anandamide and 2-arachidonoylglycerol (2-AG) modulate at the presynaptic nerve terminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521-8), thereby affecting neurotransmitter release and/or action, which decreases the release of neurotransmitter (A. C. Porter, C. C. Felder, Pharmacol. Ther., 90 (1) (2001) 45-60).

Anandamide as $\Delta^9$-THC also increases feeding through $CB_1$ receptor-mediated mechanism. $CB_1$ selective antagonists block the increase in feeding associated with administration of anandamide (C. M. Williams, T. C. Kirkham, Psychopharmacology 143 (3) (1999) 315-317; C. C. Felder, E. M. Briley, J. Axelrod, J. T. Simpson, K. Mackie, W. A. Devane, Proc. Natl. Acad. Sci. U.S.A. 90 (16) (1993) 7656-60) and caused appetite suppression and weight loss (G. Colombo, R. Agabio, G. Diaz, C. Lobina, R. Reali, G. L. Gessa, Life Sci. 63 (8) (1998) L113-PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822-825).

At least two CB1 selective antagonist/inverse agonists (SR-141716 and SLV-319) are currently undergoing clinical trials for the treatment of obesity and/or smoking cessation. In a double blind placebo-controlled study, at the doses of 10 and 20 mg daily, SR 141716 significantly reduced body weight when compared to placebo (F. Barth, M. Rinaldi-Carmona, M. Amone, H. Heshmati, G. Le Fur, "*Cannabinoid antagonists: From research tools to potential new drugs.*" Abstracts of Papers, 222nd ACS National Meeting, Chicago, Ill., United States, Aug. 26-30, 2001). SR-141716 reduced body weight, waist circumference and improved metabolic parameters (plasma HDL, triglycerides and insulin sensitivity) in several phase III studies (RIO-lipids, RIO-Europe and RIO-North America). Additionally SR-141716 has shown efficacy in a phase III trial for smoking cessation (STRATUS-US). There still remains a need for potent low molecular weight CB1 modulators that have pharmacokinetic and pharmacodynamic properties suitable for use as human pharmaceuticals.

Other compounds which have been proposed as CB1 receptor antagonists respectively inverse agonists are aminoalkylindols (AAI; M. Pacheco, S. R. Childers, R. Arnold, F. Casiano, S. J. Ward, J. Pharmacol. Exp. Ther. 257 (1) (1991) 170-183), like 6-bromo-(WIN54661; F. M. Casiano, R. Arnold, D. Haycock, J. Kuster, S. J. Ward, NIDA Res. Monogr. 105 (1991) 295-6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115-118; R. Pertwee, G. Griffin, S. Fernando, X. Li, A. Hill, A. Makriyannis, Life Sci. 56 (23-24) (1995) 1949-55). Arylbenzo[b]thiophene and benzo[b]furan (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291-7) disclosed in WO9602248, U.S. Pat. No. 5,596,106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233-2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748-1756) are known to antagonize the $CB_1$ receptor respectively act as an inverse agonist on the $hCB_1$ receptor. WO0015609 (FR2783246-A1), WO0164634 (FR2805817-A1), WO0228346, WO0164632 (FR2805818-A1), WO0164633 (FR2805810-A1) disclosed substituted 1-bis(aryl)methyl-azetidines derivatives as antagonists of $CB_1$. In WO0170700 4,5-dihydro-1H-pyrazole derivatives are described as $CB_1$ antagonists. In several patents bridged and non-bridged1,5-diphenyl-3-pyrazolecarboxamide derivatives are disclosed as $CB_1$ antagonists/inverse agonists (WO0132663, WO0046209, WO9719063, EP658546, EP656354, U.S. Pat. No. 5,624,941, EP576357, U.S. Pat. No. 3,940,418).

SUMMARY OF THE INVENTION

The present invention comprises novel pyrrole and imidazole derivatives of the general formula:

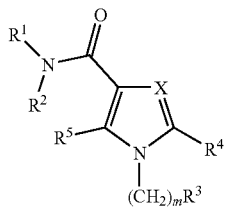

which are antagonists/inverse agonists of the CB1 receptor, their manufacture, pharmaceutical compositions containing them and their use as medicaments. The compounds of the present invention are useful in treating obesity and other disorders.

DETAILED DESCRIPTION OF THE INVENTION

The present invention comprises compounds of formula I:

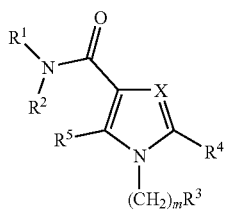

wherein
X is C—$R^6$ or N;
$R^1$ is hydrogen or lower alkyl;
$R^2$ is selected from the group consisting of lower alkyl, unsubstituted or substituted by one, two or three groups independently selected from the group consisting of hydroxy, lower alkoxy, fluorinated lower alkyl fluorinated lower alkoxy, phenyl, cycloalkyl and a 5-or 6-membered saturated heterocyclic ring containing one or two heteroatoms independently selected from nitrogen and oxygen, fluorinated lower alkyl, cycloalkyl, unsubstituted or substituted by one, two, three or four groups independently selected from the group consisting of hydroxy, lower alkyl, lower alkoxy, fluorinated lower alkyl and fluorinated lower alkoxy, a 5- or 6-membered saturated heterocyclic ring containing one or two heteroatoms independently selected from nitrogen and oxygen, said heterocyclic ring being unsubstituted or substituted by one, two or three groups independently selected from the group consisting of hydroxy, lower alkyl, lower alkoxy, amino, lower alkylamino, oxo, fluorinated lower alkyl and fluorinated lower alkoxy, bicyclo[4.1.0]hept-7-yl, unsubstituted or substituted by one, two or three groups independently selected from the group consisting of lower alkyl, hydroxy and lower alkoxy, or condensed with a phenyl ring, and 4,7,7-trimethylbicyclo[2.2.1]hept-2-yl, unsubstituted or substituted by one, two or three groups independently selected from the group consisting of hydroxy, lower alkoxy and lower acyloxy;

$R^3$ is a 5-or 6-membered saturated heterocyclic ring containing one or two heteroatoms independently selected from nitrogen or oxygen, said heterocyclic ring being unsubstituted or substituted by one, two or three groups independently selected from the group consisting of hydroxy, lower alkyl, lower alkoxy and alkoxycarbonyl, or being condensed with a phenyl ring;
$R^4$ is phenyl, unsubstituted or substituted by one, two or three groups independently selected from the group consisting of hydroxy, lower alkyl, lower alkoxy, halogen, halogenated lower alkyl and halogenated lower alkoxy;
$R^5$ is selected from the group consisting of hydrogen, lower alkyl and lower alkoxyalkyl;
$R^6$ is hydrogen or lower alkyl;
m is 1 or 2;

and pharmaceutically acceptable salts thereof.

The compounds of the present invention are selective CB1 receptor antagonists/inverse agonists. Such antagonists/inverse agonists are useful in medical therapy, particularly in the treatment and/or prevention of diseases which are associated with the modulation of CB1 receptors and particularly obesity.

Unless otherwise indicated, the following definitions are set forth to illustrate and define the meaning and scope of the various terms used to describe the invention herein.

In this specification the term "lower" is used to mean a group consisting of one to eight, preferably of one to four carbon atom(s).

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to eight carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" refers to the group R'—O—, wherein R' is lower alkyl. Examples of lower alkoxy groups are e.g. methoxy, ethoxy, propoxy, isopropoxy, butoxy, isobutoxy and hexyloxy, with methoxy being especially preferred.

The term "halogen" refers to fluorine, chlorine, bromine and iodine, preferably to chlorine and fluorine.

The term "lower alkylamino" refers to the group R'—NH—, wherein R' is lower alkyl.

The term "halogenated lower alkyl" refers to a lower alkyl group wherein at least one of the hydrogens of the lower alkyl group is replaced by a halogen atom, preferably fluoro or chloro. Among the preferred halogenated lower alkyl groups are trifluoromethyl, difluoromethyl, fluoromethyl and chloromethyl, with trifluoromethyl being especially preferred. The term "fluorinated lower alkyl" refers to a lower alkyl group wherein at least one of the hydrogens of the lower alkyl group is replaced by fluoro. Among the preferred fluorinated lower alkyl groups are trifluoromethyl, difluoromethyl, fluoromethyl and pentafluoroethyl, with trifluoromethyl or pentafluoroethyl being especially preferred.

The term "halogenated lower alkoxy" refers to a lower alkoxy group wherein at least one of the hydrogens of the lower alkoxy group is replaced by halogen, preferably by fluorine or chlorine. Among the preferred halogenated lower alkoxy groups are fluorinated lower alkoxy groups such as trifluoromethoxy, difluoromethoxy and fluoromethoxy, with trifluoromethoxy being especially preferred. The term "fluorinated lower alkoxy" refers to a lower alkoxy group wherein at least one of the hydrogens of the lower alkoxy group is replaced by fluoro. Among the preferred fluorinated lower alkoxy groups are trifluoromethoxy, difluoromethoxy and fluoromethoxy, with trifluoromethoxy being especially preferred.

The term "cycloalkyl" refers to a monovalent carbocyclic radical of three to eight, preferably three to five carbon atoms. This term is further exemplified by radicals such as cyclopropyl, cyclobutyl, cyclopentyl and cyclohexyl, with cyclohexyl being especially preferred.

The term "pharmaceutically acceptable salts" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment, the present invention relates to compounds of formula I as defined above, wherein $R^1$ is hydrogen or lower alkyl.

Preferable lower alkyl residues $R^1$ are methyl and ethyl, with methyl being especially preferred. Most preferably, $R^1$ is hydrogen.

In another embodiment, the present invention relates to compounds of formula I as defined above, wherein $R^2$ is selected from the group consisting of lower alkyl, unsubstituted or substituted by one, two or three groups independently selected from the group consisting of hydroxy, lower alkoxy, fluorinated lower alkyl, fluorinated lower alkoxy, phenyl, cycloalkyl and a 5-or 6-membered saturated heterocyclic ring containing one or two heteroatoms independently selected from nitrogen and oxygen; fluorinated lower alkyl; cycloalkyl, unsubstituted or substituted by one, two, three or four groups independently selected from the group consisting of hydroxy, lower alkyl, lower alkoxy, fluorinated lower alkyl and fluorinated lower alkoxy; a 5- or 6-membered saturated heterocyclic ring containing one or two heteroatoms independently selected from nitrogen and oxygen, said heterocyclic ring being unsubstituted or substituted by one, two or three groups independently selected from the group consisting of hydroxy, lower alkyl, lower alkoxy, amino, lower alkylamino, oxo, fluorinated lower alkyl and fluorinated lower alkoxy; bicyclo[4.1.0]hept-7-yl, unsubstituted or substituted by one, two or three groups independently selected from the group consisting of lower alkyl, hydroxy or lower alkoxy, or condensed with a phenyl ring; and 4,7,7-trimethylbicyclo[2.2.1]hept-2-yl, unsubstituted or substituted by one, two or three groups independently selected from hydroxy, lower alkoxy or lower acyloxy.

In one embodiment, the invention relates to compounds of formula I, wherein $R^2$ is lower alkyl, unsubstituted or substituted by one, two or three groups independently selected from the group consisting of hydroxy, lower alkoxy, fluorinated lower alkyl, fluorinated lower alkoxy, phenyl, cycloalkyl and a 5-or 6-membered saturated heterocyclic ring containing one or two heteroatoms independently selected from nitrogen and oxygen.

Preferable lower alkyl residues $R^2$ are branched or straight chain alkyl residues with one to eight, preferably three to five carbon atoms, such as n-propyl, isopropyl, n-butyl, s-butyl, isobutyl, n-pentyl and 2-ethylhexyl. Most preferred lower alkyl residues $R^2$ are n-propyl, n-butyl, s-butyl, isobutyl and n-pentyl, with n-butyl being especially preferred.

In a further embodiment, the invention relates to compounds of formula I wherein $R^2$ is fluorinated lower alkyl. Preferable fluorinated lower alkyl gropus are trifluormethyl and pentafluoroethyl.

In another preferred embodiment, the invention relates to compounds of formula I wherein $R^2$ is a cycloalkyl group with three to seven carbon atoms which may be unsubstituted or substituted by one, two or three groups independently selected from lower alkyl or hydroxy.

Preferable cycloalkyl residues $R^2$ are cycloalkyl residues with three to seven carbon atoms, such as cyclopropyl, cyclobutyl, cyclopentyl, cyclohexyl and cycloheptyl, which may optionally be substituted by one, two or three groups independently selected from lower alkyl or hydroxy.

Most preferable unsubstituted cycloalkyl residues $R^2$ are unsubstituted cyclopropyl, cyclobutyl, cyclopentyl and cyclohexyl, with cyclohexyl being especially preferred. Most preferable substituted cycloalkyl residues $R^2$ are cyclopropyl, cyclobutyl, cyclopentyl and cyclohexyl, with 2-hydroxy-cyclohexyl being especially preferred.

In a further preferred embodiment, the invention relates to a compound of formula I wherein $R^2$ is a 5- or 6-membered heterocyclic ring containing one or two heteroatoms independently selected from nitrogen and oxygen, said heterocyclic ring being unsubstituted or being substituted by one, two or three groups independently selected from hydroxy, lower alkyl, lower alkoxy, amino, lower alkylamino, oxo, fluorinated lower alkyl or fluorinated lower alkoxy.

Examples of heterocyclic rings $R^2$ are tetrahydrofuranyl, pyrrolidinyl, morpholinyl, piperidinyl and isoxazolidinyl, optionally substituted as defined above. Preferably, heterocyclic rings $R^2$ are unsubstituted or substituted by lower alkyl, such as methyl, or by oxo. Most preferably, $R^2$ is piperidinyl.

In a further embodiment, the present invention relates to compounds of formula I wherein $R^2$ is bicyclo[4.1.0]hept-7-yl, unsubstituted or substituted by one, two or three groups independently selected from lower alkyl, hydroxy or lower alkoxy, or condensed with a phenyl ring; or 4,7,7-trimethyl-bicyclo[2.2.1]hept-2-yl, unsubstituted or substituted by hydroxy, lower alkoxy or lower acyloxy.

More preferably, $R^2$ is selected from the following groups:

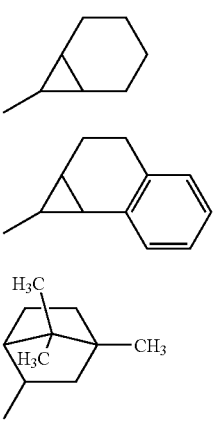

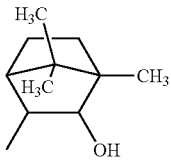

d

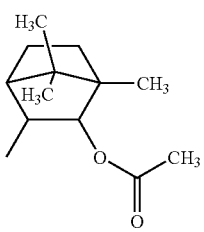

e

In another embodiment, the invention relates to compounds of formula I, wherein $R^3$ is 5-or 6-membered saturated heterocyclic ring containing one or two oxygen atoms, said heterocyclic ring being unsubstituted or being substituted by one, two or three lower alkyl groups or being condensed with a phenyl ring.

In a preferred embodiment, the invention relates to compounds of formula I, wherein $R^3$ is selected from the group consisting of tetrahydropyranyl, tetrahydrofuranyl, 2-methyl-tetrahydrofuranyl, 2,2-dimethyl-[1,3]-dioxolan-4-yl, [1,4]-dioxan-2-yl and 1-chroman-2-yl.

In another preferred embodiment, the invention relates to compounds of formula I, wherein $R^3$ is a pyrrolidine ring being unsubstituted or substituted by lower alkyl or alkoxycarbonyl.

In a further embodiment, the present invention relates to compounds of formula I, wherein $R^4$ is phenyl substituted by one, two or three groups independently selected from the group consisting of hydroxy, lower alkyl, lower alkoxy, halogen, halogenated lower alkyl and halogenated lower alkoxy.

In another embodiment, the present invention relates to compounds of formula I, wherein $R^5$ is lower alkyl, with those compounds of formula I wherein $R^5$ is methyl or ethyl being preferred, and those compounds of formula I wherein $R^5$ is methyl being especially preferred.

In one embodiment of the present invention, compounds of formula I are those wherein X is C—$R^6$ with $R^6$ being hydrogen or lower alkyl. Preferably, $R^6$ is hydrogen.

In another embodiment, the present invention relates to compounds of formula I wherein X is N.

The symbol m is 0 or 1; more preferably, m is 1.

Preferred compounds of general formula I are the following compounds:

5-methyl-1-(tetrahydro-pyran-2-ylmethyl)-2-(4-trifluoromethoxy-phenyl)-1H-imidazole-4-carboxylic acid piperidin-1-ylamide, 2-(5-chloro-2-methoxy-phenyl)-5-methyl-1-(tetrahydro-pyran-2-ylmethyl)-1H-imidazole-4-carboxylic acid cyclohexylamide, 2-(5-chloro-2-methoxy-phenyl)-5-methyl-1-(tetrahydro-pyran-2-ylmethyl)-1H-imidazole-4-carboxylic acid piperidin-1-ylamide, 2-(5-fluoro-2-methyl-phenyl)-5-methyl-1-(tetrahydro-pyran-2-ylmethyl)-1H-imidazole-4-carboxylic acid cyclohexylamide, 5-(5-chloro-2-methoxy-4-methyl-phenyl)-1-[1,4]dioxan-2-ylmethyl-2-methyl-1H-pyrrole-3-carboxylic acid piperidin-1-ylamide, 2-(2-ethoxy-phenyl)-5-methyl-1-(tetrahydro-pyran-2-ylmethyl)-1H-imidazole-4-carboxylic acid piperidin-1-ylamide, 2-methyl-1-[(S)-1-(tetrahydro-furan-2-yl)methyl]-5-(2-trifluoromethoxy-phenyl)-1H-pyrrole-3-carboxylic acid cyclohexylamide, 2-methyl-1-[(R)-1-(tetrahydro-furan-2-yl)methyl]-5-(2-trifluoromethoxy-phenyl)-1H-pyrrole-3-carboxylic acid cyclohexylamide, (rac)-1-(2,2-dimethyl-[1,3]dioxolan-4-ylmethyl)-2-methyl-5-(2-trifluoromethoxy-phenyl)-1H-pyrrole-3-carboxylic acid cyclohexylamide, (rac)-1-[1,4]dioxan-2-ylmethyl-2-methyl-5-(2-trifluoromethoxy-phenyl)-1H-pyrrole-3-carboxylic acid cyclohexylamide, 2-methyl-1-[(R)-1-(tetrahydro-furan-2-yl)methyl]-5-(2-trifluoromethoxy-phenyl)-1H-pyrrole-3-carboxylic acid ((1RS,2RS)-2-hydroxy-cyclohexyl)-amide, 2-(2,5-dichloro-phenyl)-5-methyl-1-(tetrahydro-pyran-2-ylmethyl)-1H-imidazole-4-carboxylic acid (2,2,3,3,3-pentafluoro-propyl)-amide, 2-(2-chloro-5-trifluoromethyl-phenyl)-5-methyl-1-(tetrahydro-pyran-2-ylmethyl)-1H-imidazole-4-carboxylic acid (2,2,3,3,3-pentafluoro-propyl)-amide, 2-(2-chloro-5-trifluoromethyl-phenyl)-5-methyl-1-(tetrahydro-pyran-2-ylmethyl)-1H-imidazole-4-carboxylic acid piperidin-1-ylamide, 5-(2-fluoro-5-trifluoromethyl-phenyl)-2-methyl-1-[2-(tetrahydro-pyran-4-yl)-ethyl]-1H-pyrrole-3-carboxylic acid cyclohexylamide, (rac)-1-(2,2-dimethyl-[1,3]dioxolan-4-ylmethyl)-5-(2-fluoro-5-trifluoromethyl-phenyl)-2-methyl-1H-pyrrole-3-carboxylic acid cyclohexylamide, 5-(2-fluoro-5-trifluoromethyl-phenyl)-2-methyl-1-[(S)-1-(tetrahydro-furan-2-yl)methyl]-1H-pyrrole-3-carboxylic acid ((1R,2R)-2-hydroxy-cyclohexyl)-amide, 5-(2-fluoro-5-trifluoromethyl-phenyl)-2-methyl-1-[(R)-1-(tetrahydro-furan-2-yl)methyl]-1H-pyrrole-3-carboxylic acid cyclohexylamide, 5-(2-fluoro-5-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, 1-(R)-1-chroman-2-ylmethyl-5-(2-fluoro-5-trifluoromethyl-phenyl)-2-methyl-1H-pyrrole-3-carboxylic acid cyclohexylamide, 2-[5-(5-chloro-2-fluoro-phenyl)-3-cyclohexylcarbamoyl-2-methyl-pyrrol-1-ylmethyl]-pyrrolidine-1-carboxylic acid tert-butyl ester, 1-(rac)-(2,2-dimethyl-[1,3]dioxolan-4-ylmethyl)-5-(2-fluoro-5-trifluoromethyl-phenyl)-2-methyl-1H-pyrrole-3-carboxylic acid ((1R,2R)-2-hydroxy-cyclohexyl)-amide, 5-(2,5-bis-trifluoromethyl-phenyl)-2-methyl-1-[(R)-1-(tetrahydro-furan-2-yl)methyl]-1H-pyrrole-3-carboxylic acid cyclohexylamide, 5-(2,5-bis-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, (rac)-5-(2-chloro-5-trifluoromethyl-phenyl)-1-[1,4]dioxan-2-ylmethyl-2-methyl-1H-pyrrole-3-carboxylic acid cyclohexylamide, (rac)-5-(2-chloro-5-trifluoromethyl-phenyl)-1-(2,2-dimethyl-[1,3]dioxolan-4-ylmethyl)-2-methyl-1H-pyrrole-3-carboxylic acid cyclohexylamide, 5-(2-chloro-5-trifluoromethyl-phenyl)-1-(rac)-[1,4]dioxan-2-ylmethyl-2-methyl-1H-pyrrole-3-carboxylic acid ((1R,2R)-2-hydroxy-cyclohexyl)-amide, 5-(2-chloro-5-trifluoromethyl-phenyl)-1-(rac)-(2,2-dimethyl-[1,3]dioxolan-4-ylmethyl)-2-methyl-1H-pyrrole-3-carboxylic acid ((1R,2R)-2-hydroxy-cyclohexyl)-amide, 5-(5-chloro-2-fluoro-phenyl)-2-methyl-1-pyrrolidin-2-ylmethyl-1H!-pyrrole-3-carboxylic acid cyclohexylamide; compound with trifluoro-acetic acid, (R)-2-[5-(2,5-bis-trifluoromethyl-phenyl)-3-cyclohexylcarbamoyl-2-methyl-pyrrol-1-ylmethyl]-pyrrolidine-1-carboxylic acid tert-butyl ester, (R)-2-[5-(2,5-bis-trifluoromethyl-phenyl)-3-((1R,2R)-2-hydroxy-cyclohexylcarbamoyl)-2-methyl-pyrrol-1-ylmethyl]-pyrrolidine-1-carboxylic acid tert-butyl ester, 5-(2,5-bis-trifluoromethyl-phenyl)-2-methyl-1-(R)-1-pyrrolidin-2-ylmethyl-1H-pyrrole-3-carboxylic acid cyclohexylamide; compound with trifluoro-acetic acid, 5-(2-chloro-5-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, 5-(2-chloro-5-trifluoromethyl-phenyl)-2-methyl-1-[(R)-1-(tetrahydro-furan-2-yl)methyl]-1H-pyrrole-3-carboxylic acid cyclohexylamide, 5-(2,5-bis-trifluoromethyl-phenyl)-2-methyl-1-[(R)-1-(tetrahydro-furan-2-yl)methyl]-1H-pyrrole-3-carboxylic acid bicyclo[4.1.0]hept-7-ylamide, 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-methyl-propyl)-amide, 5-(3,5-bis-trifluoromethyl-phenyl)-2-methyl--[(R)-1-(tetrahydro-furan-2-yl)methyl]-1H-pyrrole-3-carboxylic acid cyclohexylamide, 5-(3,5-bis-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, 5-(2,5-bis-trifluoromethyl-phenyl)-2-methyl-1-[(R)-1-(tetrahydro-furan-2-yl)methyl]-1H-pyrrole-3-carboxylic acid (1a,2,3,7b-tetrahydro-1H-cyclopropa[a]naphthalen-1-yl)-amide, 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-phenyl-propyl)-amide, 5-(3,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-methyl-propyl)-amide, 5-(3,5-bis-trifluoromethyl-phenyl)-2-methyl-1-[(R)-1-(tetrahydro-furan-2-yl)methyl]-1H-pyrrole-3-carboxylic acid (1S,6R)-bicyclo[4.1.0]hept-7-ylamide, 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-1-methyl-propyl)-amide, 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-1-methyl-propyl)-amide, (R)-2-[5-(3,5-bis-trifluoromethyl-phenyl)-3-cyclohexylcarbamoyl-2-methyl-pyrrol-1-ylmethyl]-pyrrolidine-1-carboxylic acid tert-butyl ester, (S)-2-[5-(2,5-bis-trifluoromethyl-phenyl)-3-cyclohexylcarbamoyl-2-methyl-pyrrol-1-ylmethyl]-pyrrolidine-1-carboxylic acid tert-butyl ester, 5-(2,5-bis-trifluoromethyl-phenyl)-2-methyl-1-[(R)-1-(tetrahydro-furan-2-yl)methyl]-1H-pyrrole-3-carboxylic acid (2-methoxy-1-methyl-2-phenyl-ethyl)-amide, 5-(2,5-bis-trifluoromethyl-phenyl)-2-methyl-1-[(R)-1-(tetrahydro-furan-2-yl)methyl]-1H-pyrrole-3-carboxylic acid (3-methoxy-4,7,7-trimethyl-bicyclo[2.2.1]hept-2-yl)-amide, acetic acid 3-({5-(2,5-bis-trifluoromethyl-phenyl)-2-methyl-1-[(R)-1-(tetrahydro-furan-2-yl)methyl]-1H-pyrrole-3-carbonyl}-amino)-1,7,7-trimethyl-bicyclo [2.2.1]hept-2-yl ester, 5-(2,5-bis-trifluoromethyl-phenyl)-2-methyl-1-[(R)-1-(tetrahydro-furan-2-yl)methyl]-1H-pyrrole-3-carboxylic acid (2-hydroxy-2-methyl-propyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-hydroxy-2-phenyl-propyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-hydroxy-3-methoxy-propyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-methoxy-2-phenyl-ethyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-hydroxy-2-phenyl-ethyl)-amide, 5-(2,5-bis-trifluoromethyl-phenyl)-2-methyl--[(R)-1-(tetrahydro-furan-2-yl)methyl]-1H-pyrrole-3-carboxylic acid (2-hydroxy-3-morpholin-4-yl-propyl)-amide, 5-(3,5-bis-trifluoromethyl-phenyl)-2-methyl-1-(R)-1-pyrrolidin-2-ylmethyl-1H-pyrrole-3-carboxylic acid cyclohexylamide, 5-(2,5-bis-trifluoromethyl-phenyl)-2-methyl-1-(S)-1-pyrrolidin-2-ylmethyl-1H-pyrrole-3-carboxylic acid cyclohexylamide, 5-(2,5-bis-trifluoromethyl-phenyl)-2-methyl-1-[(R)-1-(tetrahydro-furan-2-yl)methyl]-1H-pyrrole-3-carboxylic acid (3-hydroxy-4,7,7-trimethyl-bicyclo[2.2.1]hept-2-yl)-amide, 5-(2-chloro-5-trifluoromethyl-phenyl)-2-methyl-1-((S)-2-methyl-tetrahydro-furan-2-ylmethyl)-1H-pyrrole-3-carboxylic acid ((1R,2R)-2-hydroxy-cyclohexyl)-amide, 5-(2-chloro-5-trifluoromethyl-phenyl)-2-methyl-1-((R)-2-methyl-tetrahydro-furan-2-ylmethyl)-1H-pyrrole-3-carboxylic acid ((1R,2R)-2-hydroxy-cyclohexyl)-amide, 5-(2-chloro-5-trifluoromethyl-phenyl)-2-methoxymethyl-1-[(R)-1-(tetrahydro-furan-2-yl)methyl]-1H-pyrrole-3-carboxylic acid cyclohexylamide, 5-(2,5-bis-trifluoromethyl-phenyl)-2-methyl-1-[(R)-1-(tetrahydro-furan-2-yl)methyl]-1H-pyrrole-3-carboxylic acid ((S)-2-hydroxy-2-phenyl-ethyl)-amide, 5-(2,5-bis-trifluoromethyl-phenyl)-1-[1,4]dioxan-2-ylmethyl-2-methyl-1H-pyrrole-3-carboxylic acid ((1R,2R)-2-hydroxy-cyclohexyl)-amide, 5-(2,5-bis-trifluoromethyl-phenyl)-1-[1,4]dioxan-2-ylmethyl-2-methyl-1H-pyrrole-3-carboxylic acid (2-hydroxy-2-phenyl-propyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-ethyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-propyl)-amide, 5-(3,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-propyl)-amide, 5-(3,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide, 5-(3,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide, and pharmaceutically acceptable salts thereof.

Especially preferred are the compounds selected from the group consisting of:

5-(2-fluoro-5-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, 5-(3,5-bis-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, 5-(2,5-bis-trifluoromethyl-phenyl)-2-methyl-1-[(R)-1-(tetrahydro-furan-2-yl)methyl]-1H-pyrrole-3-carboxylic acid (1a,2,3,7b-tetrahydro-1H-cyclopropa [a]naphthalen-1-yl)-amide, 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-phenyl-propyl)-amide, 5-(2,5-bis-trifluoromethyl-phenyl)-1-[1,4]dioxan-2-ylmethyl-2-methyl-1H-pyrrole-3-carboxylic acid ((1R,2R)-2-hydroxy-cyclohexyl)-amide, 5-(2,5-bis-trifluoromethyl-phenyl)-1-[1,4]dioxan-2-ylmethyl-2-methyl-1H-pyrrole-3-carboxylic acid (2-hydroxy-2-phenyl-propyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-propyl)-amide, and pharmaceutically acceptable salts thereof.

The present invention also relates to a process for the manufacture of compounds of formula I as defined above, which process comprises:

where X is C—$R^6$, reaction of an enamine of formula A

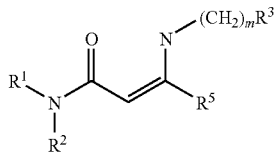

A wherein $R^1$, $R^2$, $R^3$, $R^5$ and m are as defined above;
with an alfa-bromoketone of formula B

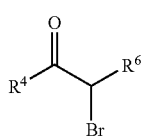

B wherein $R^4$ and $R^6$ are as defined above; or
where X is N, alkylation of an imidazole of formula F

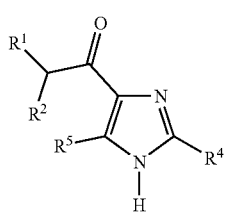

F wherein $R^1$, $R^2$, $R^4$ and $R^5$ are as defined claim 1;
with an alkyl bromide of formula G

G wherein $R^3$ and m are as defined above; or
where X is C, reaction of a carboxylic acid of formula N

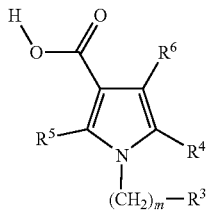

N wherein $R^3$, $R^4$, $R^5$, $R^6$ and m are as defined above;
with an amine of formula J

J wherein $R^1$ and $R^2$ are as defined above;

and, if desired, converting the resulting compound of formula I into a pharmaceutically acceptable salt thereof.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

Compounds of formula I having the formula Ia, wherein $R^1$ to $R^6$ and m are as previously defined and X is C—$R^6$, can be prepared by reaction of enamines of formula A with alpha-bromoketones of formula B according to methods known in the art (Scheme 1). For example, the reaction can be performed in an inert solvent, such as DMF, in the presence of a hindered base, such as 2,6-di-tert-butylpyridine or 2,6-lutidine.

Scheme 1

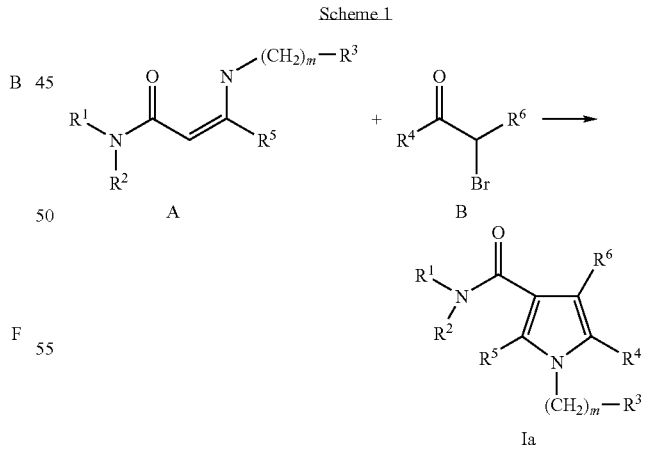

Enamines of formula A can be prepared from beta-ketoamides of formula C and amines of formula D by methods known in the art (Scheme 2). For example a beta-keto amide of formula C can be reacted with an amine of formula D in a suitable inert solvent (e.g. DMF) in the presence of a hindered base (e.g. 2,6-di-tert-butylpyridine) to yield enamine of formula A.

Scheme 2

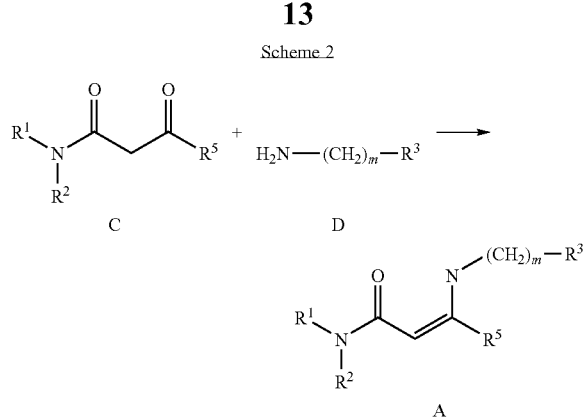

Beta-ketoamides of formula C can be purchased from commercial sources or can be prepared by methods known in the art. For example, beta-ketoamides of formula C wherein $R^5$ is methyl can be prepared by reaction of amines of formula E with diketene in an inert solvent, such as dichloromethane (Scheme 3).

Scheme 3

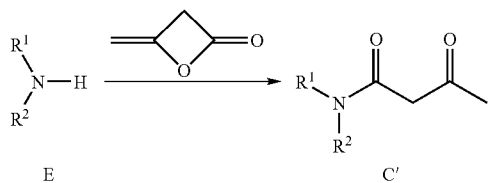

Compounds of formulae B and D are either known from the literature or can be purchased from commercial sources or else can be synthesized by methods known in the art.

Compounds of formula I having the formula Ib, wherein $R^1$ to $R^6$ and m are as previously defined and X is N, can be prepared by alkylation of imidazoles of formula F according to methods known in the art (Scheme 4). For example, imidazoles of formula F may be reacted with alkyl bromides of formula G in the presence of a base (e.g. potassium tert-butylate) in an inert solvent, such as acetonitrile.

Scheme 4

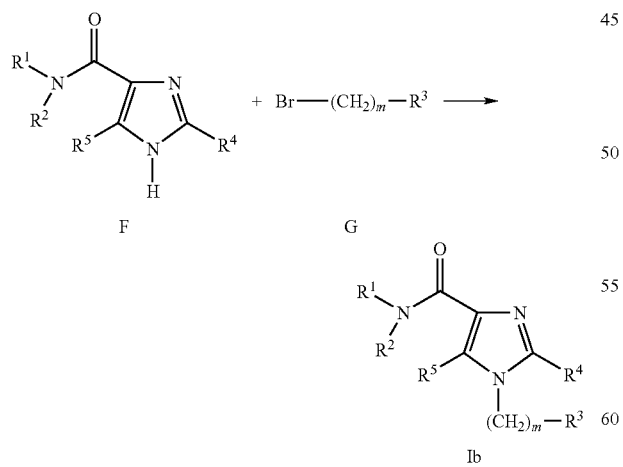

Compounds of formula H can be coupled with an appropriate amine of formula J by methods known in the art (Scheme 5). The reaction can be performed in a suitable inert solvent (e.g. DMF, dichloromethane, pyridine or THF) in the presence of a base (e.g. Hünigs' base) and an activating agent (e.g. TBTU=O-(Benzotriazol-1-yl)-N,N',N'-tetramethyl-uronium-tetrafluoroborat) to yield the corresponding amides of formula F.

Scheme 5

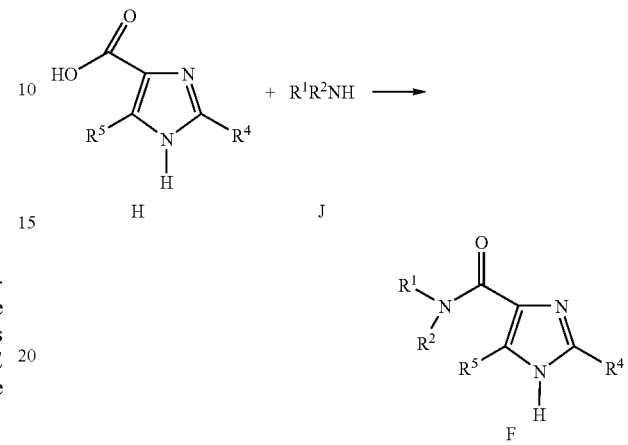

Compounds of formula H can be obtained by hydrolysis of compounds of formula K by methods known in the art (Scheme 6). For example, the reaction can proceed in a polar solvent (e.g. ethanol) in the presence of a base (e.g. sodium hydroxide).

Scheme 6

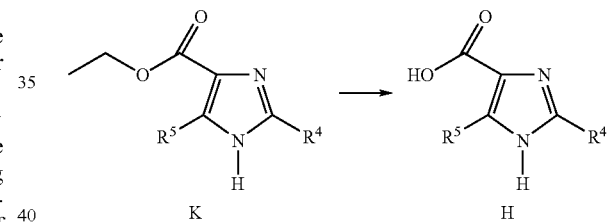

Imidazoles of formula K can be prepared by the reation of 2-oximinoacetoacetates of formula L with an appropriate amine of formula M by methods known in the art (Scheme 7). For example, the reaction can proceed in a polar solvent (e.g. acetonitrile) at elevated temperature.

Scheme 7

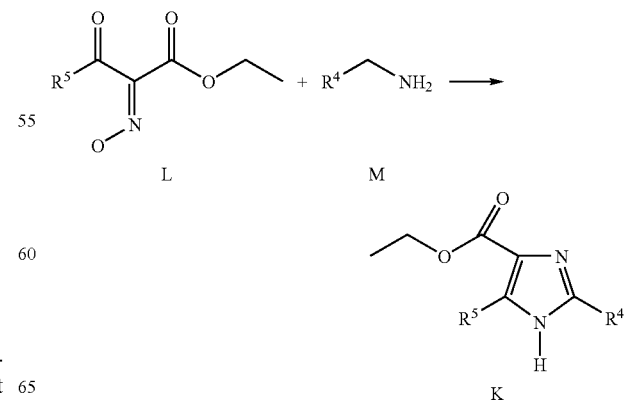

Compounds of formula G, J, L and M are either known from the literature or can be purchased from commercial sources or else can be synthesized by methods known in the art.

Alternatively, compounds of formula I having the formula Ia, wherein $R^1$ to $R^6$ and m are as previously defined and X is C—$R^6$, can also be prepared from compounds of formula N by coupling with an appropriate amine of formula J by methods known in the art (Scheme 8). The reaction can be performed in a suitable inert solvent (e.g. DMF, dichloromethane, pyridine or THF) in the presence of a base (e.g. Hünigs' base) and an activating agent (e.g. TBTU=O-(Benzotriazol-1-yl)-N,N',N'-tetramethyl-uronium-tetrafluoroborate) to yield the corresponding amides of formula Ia.

Scheme 8

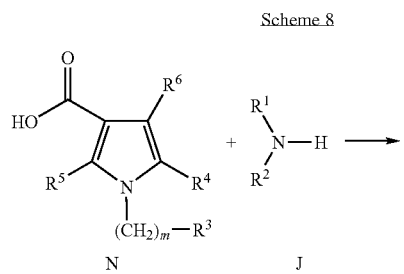

Compounds of formula N can be obtained by hydrolysis of compounds of formula O by methods known in the art (Scheme 9). For example, the reaction can proceed in a polar solvent (e.g. ethanol) in the presence of base (e.g. sodium hydroxide).

Scheme 9

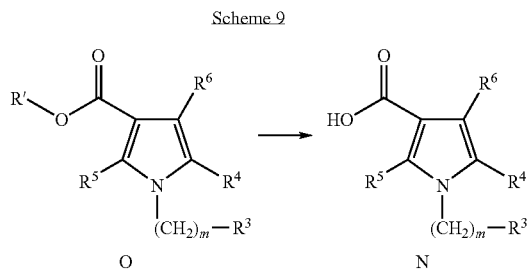

Compounds of formula O, wherein R' n be prepared by methods known in the art as exemplified in Scheme 10. For example they can be prepared by the condensation of amines or anilines of formula Q with 1,4-diketones of formula P.

Amines or anilines of formula Q are either known from the literature or can be purchased from commercial sources or else can be synthesized by methods know in the art.

Scheme 10

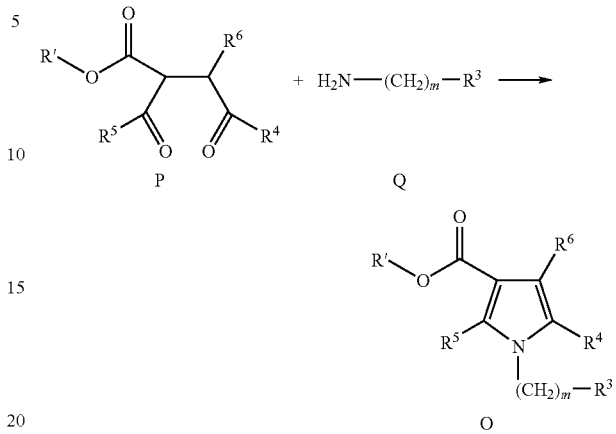

Diketones of formula P can be prepared by methods known from the literature. For example they can be produced by the reaction of ketoesters of formula R with bromoketones of formula S (Scheme 11).

Scheme 11

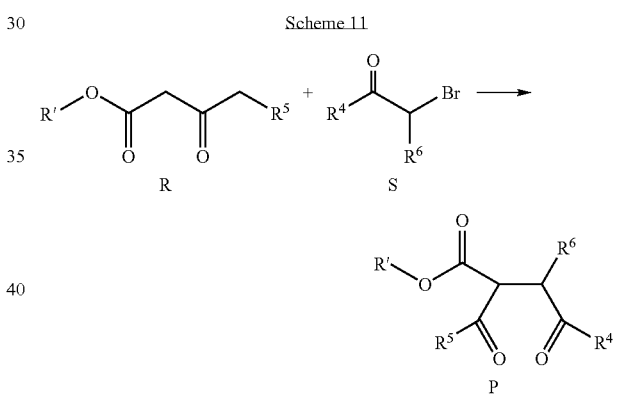

Ketoesters of formula R, wherein R' is methyl or ethyl, are either known from the literature or can be purchased from commercial sources or else can be synthesized by methods know in the art.

Bromoketones of formula S are either known from the literature or can be purchased from commercial sources or else can be synthesized by methods known in the art. For example they can be synthesized from the corresponding ketones of formula V by bromination methods using for example bromine or $CuBr_2$.

Ketones of formula V are either known from the literature or can be purchased from commercial sources or else can be synthesized by methods known in the art. For example the ketones of formula V can be produced from the corresponding carboxylic acids or acyl halides of formula T in two steps via Weinreb's amide of formula V.

Carboxylic acids of formula T are either known from the literature or can be purchased from commercial sources or else can be synthesized by methods know in the art.

Scheme 12

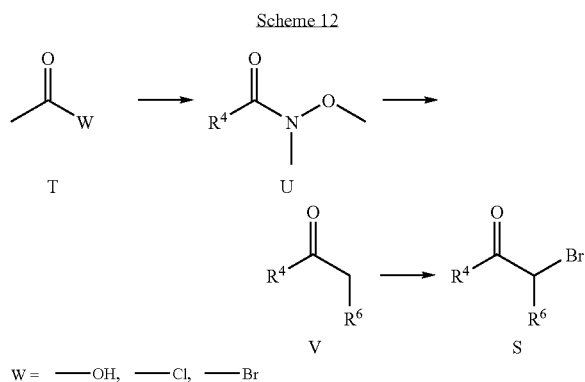

W = —OH, —Cl, —Br

The invention further relates to compounds of formula I as defined above, when manufactured according to a process as defined above.

Some compounds of formula I may possess asymmetric centres and are therefore capable of existing in more than one stereoisomeric form. The invention thus also relates to compounds in substantially pure isomeric form at one or more asymmetric centres as well as mixtures, including racemic mixtures, thereof. Such isomers may be prepared by asymmetric synthesis, for example using chiral intermediates, or mixtures may be resolved by conventional methods, eg., chromatography (chromatography with a chiral adsorbens or eluent), or use of a solving agent.

It will be appreciated, that the compounds of general formula I in this invention may be derivatised at functional groups to provide derivatives which are capable of conversion back to the parent compound in vivo.

As described above, the compounds of formula I or pharmaceutically acceptable salts thereof can be used as medicaments for the treatment and/or prophylaxis of diseases which are associated with the modulation of the CB1 receptors.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with the modulation of CB1 receptors.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments for the treatment and/or prophylaxis of diseases which are associated with the modulation of CB1 receptors. Such medicaments comprise a compound as defined above.

In this context, the expression diseases 'associated with modulation of CB1 receptors' means diseases which can be treated and/or prevented by modulation of CB1 receptors. Such diseases encompass, but are not limited to, psychic disorders, especially anxiety, psychosis, schizophrenia, depression, abuse of psychotropes, for example for the abuse and/or dependence of a substances, including alcohol dependency and nicotine dependency, neuropathies, multiple sclerosis, migraine, stress, epilepsy, dyskinesias, Parkinson's disease, amnesia, cognitive disorders, memory deficits, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, neuroinflammation, in particular in atherosclerosis, or the Guillain-Barré syndrome, viral encephalitis, cerebral vascular incidents and cranial trauma.

In a preferable aspect, the expression 'diseases associated with modulation of CB1 receptors' relates to eating disorders, obesity, diabetes type II or non insulin dependent diabetes (NIDD), neuroinflammation, diarrhea, abuse and/or dependence of a substances, including alcohol dependency and nicotine dependency. In a more preferable aspect, the said term related to eating disorders, obesity, diabetes type II or non insulin dependent diabetes (NIDD), abuse and/or dependence of a substances, including alcohol dependency and nicotine dependency, with obesity being especially preferred.

It is a further preferred object to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

It is a further preferred object to provide a method of treatment or prevention of Type II diabetes (non-insulin dependent diabetes mellitus (NIDDM) in a human which comprises administration of a therapeutically effective amount of a compound according to formula I in combination or association with a therapeutically effective amount of a lipase inhibitor, particularly, wherein the lipase inhibitor is orlistat. Also an object of the invention is the method as described above for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM) in a human which comprises administration of a therapeutically effective amount of a compound according to formula I in combination or association with a therapeutically effective amount of an anti-diabetic agent selected from the group consisting of 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331, and the like 5) DPP-IV-inhibitors such as LAF-237 (Vildagliptin) or MK-0431, and the like; 6) Glucokinase activators such as the compounds disclosed in e.g. WO 00/58293 A1, and the like. Also an object of the invention is the method as described above for the simultaneous, separate or sequential administration of a compound according to formula I and a therapeutically effective amount of an anti-diabetic agent as 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331 GW-2331 and the like; 5) DPP-IV-inhibitors such as LAF-237 (Vildagliptin) or MK-0431, and the like; 6) Glucokinase activators such as the compounds disclosed in e.g. WO 00/58293 A1, and the like.

It is a further preferred object to provide a method of treatment or prevention of dyslipidemias in a human which comprises administration of a therapeutically effective amount of a compound according to formula I in combination or association with a therapeutically effective amount of a lipid lowering agent as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists. Also an object of the invention is the method as described above for the simultaneous, separate or sequential administration of a compound according to formula I and a therapeutically effective amount of a lipid lowering agent as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149-153, 1990; Morris, J. Neurosci. Methods 11:47-60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442-448, 2002; Campbell et al., Exp. Clin. Psychopharmacol. 8:312-25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior.

The following tests were carried out in order to determine the activity of the compounds of formula I.

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glass-fiber filters. Radioactivity on the filter was measured by liquid scintillation counting. The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintillation counting. The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature 1990, 346, 561-564 (CB1) and Nature 1993, 365, 61-65 (CB2) respectively. Adenylyl cyclase was stimulated using forskolin and measured by quantifying the amount of accumulated cyclic AMP. Concomitant activation of CB1 receptors by CB1 receptor agonists (e.g. CP-55,940 or (R)-WIN-55212-2) can attenuate the forskolin-induced accumulation of cAMP in a concentration dependent manner. This CB1 receptor mediated response can be antagonised by CB1 receptor antagonists such as the compounds of the invention.

The compounds of formula (I) show an excellent affinity for the CB1 receptor, determined with the experimental conditions described in Devane et. al. Mol. Pharmacol. 34 (1988) 605-613. They also exhibit at least a 10 fold selectivity against the CB2 receptor. The compounds of the present invention or their pharmaceutically acceptable salts are antagonists and selective for the CB1 receptor with affinites below $IC_{50}=2$ µM, preferably 1 nM to 100 nM. The Table below provides representative $IC_{50}$ data from three compounds from the Examples:

| Compound of Example | $IC_{50}$ [µM] |
|---|---|
| 1 | 0.12 |
| 10 | 0.076 |
| 23 | 0.008 |

Effect of CB1 Receptor Antagonist/Inverse Agonist on CP 55,940-induced Hypothermia in NMRI Mice:

Animals

Male NMRI mice were used in this study and were obtained from Research Consulting Company Ltd (RCC) of Füllinsdorf (Switzerland). Mice, weighing 30-31 g were used in this study. Ambient temperature is approximately 20-21° C. and relative humidity 55-65%. A 12 hours light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense n°8528-20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

The in vivo activity of compounds of formula (1) was assessed for their ability to regulate feeding behaviour by recording food consumption in food deprived animals:

Rats were trained to have access to food for 2 h per day and were food deprived for 22 h. When they were trained under this schedule, the amount of food taken every day during these 2 h food intake session was consistent day after day.

To test the ability of compounds of formula I to decrease food intake, 8 animals were used in a cross-over study. Rats were individually housed in Plexiglas boxes with a grid on the floor and a paper was placed below the cage floor to collect any spillage. A food dispenser (becher) filled with a preweighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. *$P<0.05$ compared to Saline-treated rats.

Furthermore the utility of compounds of formula I in diseases or disorders may be demonstrated in animal disease models that have been reported in the literature. The following are examples of such animal disease models: a) reduction of sweet food intake in marmosets (Behavioural Pharm, 1998, 9,179-181); b) reduction of sucrose and ethanol intake in mice (Psychopharm. 1997, 132, 104-106); c) increased motor activity and place conditioning in rats (Psychopharm. 1998, 135, 324-332; Psychopharmacol 2000, 151:25-30); d) spontaneous locomotor activity in mice (J. Pharm. Exp. Ther. 1996, 277, 586-594); e) reduction in opiate self-administration in mice (Sci. 1999, 283, 401-404).

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

MS=mass spectrometry; ISP=ion spray (positive ion), corresponds to ESI (electrospray, positive ion); mp=melting point; TBTU=O-(Benzotriazol-1-yl)-N,N',N'-tetramethyluronium-tetrafluoroborate; DMF=dimethylformamide.

Example 1

5-Methyl-1-(tetrahydro-pyran-2-ylmethyl)-2-(4-trifluoromethoxy-phenyl)-1H-imidazole-4-carboxylic acid piperidin-1-ylamide Preparation of 5-methyl-2-(4-trifluoromethoxy-phenyl)-1H-imidazole-4-carboxylic acid ethyl ester To a solution of 7.9 g of ethyl 2-oximinoacetoacetate in acetonitrile (100 ml) was added 10.5 g of 4-(trifluoromethoxy)benzylamine (as $R^4$—$CH_2$—$NH_2$). The reaction mixture was then refluxed for 17 hours under argon atmosphere. After such time the reaction mixture was cooled down to 0° C., the solid was filtered off, washed with acetonitrile, and dried in vacuo to yield 11.2 g of a light yellow powder, MS (ISP) 315 (M+H)$^+$.

Preparation of 5-methyl-2-(4-trifluoromethoxy-phenyl)-1H-imidazole-4-carboxylic acid To 11.0 g of 5-methyl-2-(4-trifluoromethoxy-phenyl)-1H-imidazole-4-carboxylic acid ethyl ester in 40 ml of ethanol was added 40 ml of a 2N—NaOH solution and the reaction mixture was stirred at 100° C. for 17 hours. After such time the reaction mixture was cooled to +5° C. and treated with 80 ml of a 1N HCl solution. The precipitate was filtered, washed with water and dried under high vacuo to yield 8.3 g of a white powder.

Preparation of 5-methyl-2-(4-trifluoromethoxy-phenyl)-1H-imidazole-4-carboxylic acid piperidin-1-ylamide To 1 g of 5-methyl-2-(4-trifluoromethoxy-phenyl)-1H-imidazole-4-carboxylic acid in 50 ml of DMF was added 1.12 g of TBTU and 3.0 ml of Hünigs' base and the reaction mixture was stirred for 1 minute. Then 0.38 ml of 1-aminopiperidine (as $R^1R^2NH$) was added and the reaction mixture was stirred for 4.5 hour at room temperature. After such time the reaction mixture was poured onto 250 ml of water and extracted with ethyl acetate (2×200 ml). The combined organic extracts were then washed with water (2×100 ml) and brine (50 ml), dried (MgSO$_4$) and after filtration, concentrated in vacuo to yield an oil which crystallized during concentration. The residue (about 30 ml volume) was then treated with heptane (200 ml), the solid was filtered and dried to yield 1.15 g of the title compound, MS (ISP) 369.0 (M+H)$^+$.

Preparation of 5-Methyl-1-(tetrahydro-pyran-2-ylmethyl)-2-(4-trifluoromethoxy-phenyl)-1H-imidazole-4-carboxylic acid piperidin-1-ylamide To a suspension of 100 mg of 5-methyl-2-(4-trifluoromethoxy-phenyl)-1H-imidazole-4-carboxylic acid piperidin-1-ylamide in 3 ml of acetonitrile was added 33 mg of potassium tert-butylate and the reaction mixture was stirred at room temperature for 2 minutes. After such time, 0.034 ml of 2-(bromomethyl)-tetrahydro-2H-pyran (as $R^3$—$(CH_2)_m$—Br) was added and the reaction mixture was stirred at 100° C. for 26 hours under argon atmosphere. The reaction mixture was then diluted with ethylacetate/water, the aqueous phase removed, and the organic phase was washed with 2×H$_2$O followed by brine, dried (MgSO4), and after filtration concentrated in vacuo and purified by column chromatography (50 g SiO$_2$, CH$_2$Cl$_2$/MeOH: 24/1) to give 44 mg of the title compound as a pale yellow solid, MS (ISP) 467.2 (M+H)$^+$.

Examples 2-4, 6, and 12-14 were synthesized in analogy to example 1, using the indicated starting materials.

Example 2

2-(5-Chloro-2-methoxy-phenyl)-5-methyl-1-(tetrahydro-pyran-2-ylmethyl)-1H-imidazole-4-carboxylic acid cyclohexylamide The title compound was obtained in analogy to example 1, using 5-chloro-2-methoxybenzylamine as $R^4$—$CH_2$—$NH_2$, cydohexylamine as $R^1R^2NH$ and 2-(bromomethyl)tetrahydro-2H-pyran as $R^3$—$(CH_2)_m$—Br, MS (ISP): 446.2 (M+H)$^+$.

Example 3

2-(5-Chloro-2-methoxy-phenyl)-5-methyl-1-(tetrahydro-pyran-2-ylmethyl)-1H-imidazole-4-carboxylic acid piperidin-1-ylamide The title compound was obtained in analogy to example 1, using 5-chloro-2-methoxybenzylamine as $R^4$—$CH_2$—$NH_2$, 1-aminopiperidine as $R^1R^2NH$ and 2-(bromomethyl)tetrahydro-2H-pyran as $R^3$—$(CH_2)_m$—Br, MS (ISP): 447.2 (M+H)$^+$.

Example 4

2-(5-Fluoro-2-methyl-phenyl)-5-methyl-1-(tetrahydro-pyran-2-ylmethyl)-1H-imidazole-4-carboxylic acid cyclohexylamide The title compound was obtained in analogy to example 1, using 5-fluoro-2-methylbenzylamine as $R^4$—$CH_2$—$NH_2$, cyclohexylamine as $R^1R^2NH$ and 2-(bromomethyl)tetrahydro-2H-pyran as $R^3$—$(CH_2)_m$—Br, MS (ISP): 414.3 (M+H)+.

Example 5

Rac-5-(5-Chloro-2-methoxy-4-methyl-phenyl)-1-[1,4]dioxan-2-ylmethyl-2-methyl-1H-pyrrole-3-carboxylic acid piperidin-1-ylamide The title compound was synthesized in analogy to Example 7, using 3-oxo-butyric acid methyl ester as compound of formula R, 2-bromo-1-(5-chloro-2-methoxy-4-methyl-phenyl)-ethanone (purchased from Oakwood) as compound of formula S, rac-1,4-dioxane-2-methanamine as $R^3$—$(CH_2)_m$—$NH_2$ and piperidine-1-ylamine as $R^1R^2NH$, MS (ISP) 462.2 (M+H)$^+$.

Example 6

2-(2-Ethoxy-phenyl)-5-methyl-1-(tetrahydro-pyran-2-ylmethyl)-1H-imidazole-4-carboxylic acid piperidin-1-ylamide The title compound was obtained in analogy to example 1, using 2-ethoxybenzylamine as $R^4$—$CH_2$—$NH_2$, 1-aminopiperidine as $R^1R^2NH$ and 2-(bromomethyl)tetrahydro-2H-pyran as $R^3$—$(CH_2)_m$—Br, MS (ISP): 427.3 (M+H)$^+$.

Example 7

2-Methyl-1-[(S)-1-(tetrahydro-furan-2-yl)methyl]-5-(2-trifluoromethoxy-phenyl)-1H-pyrrole-3-carboxylic acid cyclohexylamide Preparation of 3-oxo-2-[2-oxo-2-(2-trifluoromethoxy-phenyl)-ethyl]-butyric acid methyl ester To a solution of 2.6 g of 3-oxo-butyric acid methyl ester in THF (50 ml) and 4.6 ml of a solution of sodium methoxide (5.4 M in methanol) was added over 15 minutes a solution of 6.7 g of 2-bromo-1-[2-(trifluoromethoxy)phenyl]-ethanone in 30 ml of THF. The reaction mixture was allowed to stir at room temperature for 17 hours. The solvent was removed, the residue was diluted in diethyl ether and washed several times with water. The organic phase was dried with sodium sulfate and concentrated in vacuo. The residue was purified by column chromatography (silica gel; heptane/ethyl acetate) to give 5.1 g of the title compound. MS (EI) 319.1 (M+H)+.

Preparation of 2-methyl-1-[(S)-1-(tetrahydro-furan-2-yl)methyl]-5-(2-trifluoromethoxy-phenyl)-1H-pyrrole-3-carboxylic acid methyl ester To a solution of 250 mg of 3-oxo-2-[2-oxo-2-(2-trifluoromethoxy-phenyl)-ethyl]-butyric acid methyl ester in methanol was added 84 µl of (S)-tetrahydrofurfurylamine and 5 mg of p-toluene sulfonic acid. The reaction mixture was then heated at reflux for 24 hours. After such time the reaction mixture was allowed to cool to room temperature before being concentrated in vacuo and purified by column chromatography to give 171 mg of the title compound; MS (EI) 383.1 (M)$^+$.

Preparation of 2-methyl-1-[(S)-1-(tetrahydro-furan-2-yl)methyl]-5-(2-trifluoromethoxy-phenyl)-1H-pyrrole-3-carboxylic acid To a solution of 171 mg of 2-methyl-1-[(S)-1-(tetrahydro-furan-2-yl)methyl]-5-(2-trifluoromethoxy-phenyl)-1H-pyrrole-3-carboxylic acid methyl ester in dioxane (4 ml) and water (4 ml) was added 1.3 ml of a 1N solution of sodium hydroxide. The reaction mixture was heated at reflux for 20 hours. After such time the reaction mixture was allowed to cool down to room temperature. The mixture was diluted with diethyl ether and extracted with 1N sodium hydroxide solution. Water phases were pooled, acidified with 2N solution of hydrochloride acid and extracted twice with diethyl ether. The organic phases were pooled, washed with brine and dried with MgSO$_4$. Solvent was removed to give 154 mg of the title compound as brownish oil; MS (ISP) 368.0 (M–H).

Preparation of 2-methyl-1-[(S)-1-(tetrahydro-furan-2-yl)methyl]-5-(2-trifluoromethoxy-phenyl)-1H-pyrrole-3-carboxylic acid cyclohexylamide To a solution of 77 mg of 2-methyl-1-[(S)-1-(tetrahydro-furan-2-yl)methyl]-5-(2-trifluoromethoxy-phenyl)-1H-pyrrole-3-carboxylic acid in 3 ml of dimethylformamide were added 74 mg of TBTU, 179 µl of N,N-diisopropylethylamine and 26 µl of cyclohexylamine and the reaction mixture was stirred at ambient temperature for 18 hours. After such time the reaction mixture was then concentrated in vacuo and purified by column chromatography (SiO2, heptane/ethyl acetate) to give 70 mg of the title compound as a colorless solid, MS (ISP) 451.5 (M+H)+.

Example 8

2-Methyl-1-[(R)-1-(tetrahydro-furan-2-yl)methyl]-5-(2-trifluoromethoxy-phenyl)-1H-pyrrole-3-carboxylic acid cyclohexylamide The title compound was synthesized in analogy to example 7, using 3-oxo-butyric acid methyl ester as compound of formula R, 2-bromo-1-[2-(trifluoromethoxy)phenyl]-ethanone as compound of formula S, (R)-tetrahydrofurfurylamine as $R^3$—$(CH_2)_m$—$NH_2$ and cyclohexylamine as $R^1R^2NH$, MS (ISP) 451.5 (M+H)$^+$.

Example 9

(rac)-1-(2,2-Dimethyl-[1,3]dioxolan-4-ylmethyl)-2-methyl-5-(2-trifluoromethoxy-phenyl)-1H-pyrrole-3-carboxylic acid cyclohexylamide The title compound was synthesized in analogy to example 7, using 3-oxo-butyric acid methyl ester as compound of formula R, 2-bromo-1-[2-(trifluoromethoxy)phenyl]-ethanone as compound of formula S, 2,2-dimethyl-1,3-dioxolan-4-methylamine as $R^3$—$(CH_2)_m$—$NH_2$ and cyclohexylamine as $R^1R^2NH$, MS (ISP) 481.5 $(M+H)^+$.

Example 10

(rac) 1-[1,4]Dioxan-2-ylmethyl-2-methyl-5-(2-trifluoromethoxy-phenyl)-1H-pyrrole-3-carboxylic acid cyclohexylamide The title compound was synthesized in analogy to example 7, using 3-oxo-butyric acid methyl ester as compound of formula R, 2-bromo-1-[2-(trifluoromethoxy)phenyl]-ethanone as compound of formula S, 1,4-dioxane-2-methanamine as $R^3$—$(CH_2)_m$—$NH_2$ and cyclohexylamine as $R^1R^2NH$, MS (ISP) 467.5 $(M+H)^+$.

Example 11

2-Methyl-1-[(R)-1-(tetrahydro-furan-2-yl)methyl]-5-(2-trifluoromethoxy-phenyl)-1H-pyrrole-3-carboxylic acid ((1RS,2RS)-2-hydroxy-cyclohexyl)-amide The title compound was synthesized in analogy to example 7, using 3-oxo-butyric acid methyl ester as compound of formula R, 2-bromo-1-[2-(trifluoromethoxy)phenyl]-ethanone as compound of formula S, (R)-tetrahydrofurfurylamine as $R^3$—$(CH_2)_m$—$NH_2$ and trans-2-aminocyclohexanol as $R^1R^2NH$, MS (ISP) 467.5 $(M+H)^+$.

Example 12

2-(2,5-Dichloro-phenyl)-5-methyl-1-(tetrahydro-pyran-2-ylmethyl)-1H-imidazole-4-carboxylic acid (2,2,3,3,3-pentafluoro-propyl)-amide The title compound was obtained in analogy to example 1, using 2,5-dichlorobenzylamine as $R^4$—$CH_2$—$NH_2$, 2,2,3,3,3-pentafluoro-propylamine as $R^1R^2NH$ and 2-(bromomethyl)-tetrahydro-2H-pyran as $R^3$—$(CH_2)_m$—Br, MS (ISP): 500 $(M+H)^+$.

Example 13

2-(2-Chloro-5-trifluoromethyl-phenyl)-5-methyl-1-(tetrahydro-pyran-2-ylmethyl)-1H-imidazole-4-carboxylic acid (2,2,3,3,3-pentafluoro-propyl)-amide The title compound was obtained in analogy to example 1, using 2-chloro-5-trifluoromethyl-benzylamine as $R^4$—$CH_2$—$NH_2$, 2,2,3,3,3-pentafluoro-propylamine as $R^1R^2NH$ and 2-(bromomethyl)tetrahydro-2H-pyran as $R^3$—$(CH_2)_m$—Br, MS (ISP): 534 $(M+H)^+$.

Example 14

2-(2-Chloro-5-trifluoromethyl-phenyl)-5-methyl-1-(tetrahydro-pyran-2-ylmethyl)-1H-imidazole-4-carboxylic acid piperidin-1-ylamide The title compound was obtained in analogy to example 1, using 2-chloro-5-trifluoro-methyl-benzylamine as $R^4$—$CH_2$—$NH_2$, 1-aminopiperidine as $R^1R^2NH$ and 2-(bromo-methyl)-tetrahydro-2H-pyran as $R^3$—$(CH_2)_m$—Br, MS (ISP): 485 $(M+H)^+$.

Example 15

5-(2-Fluoro-5-trifluoromethyl-phenyl)-2-methyl-1-[2-(tetrahydro-pyran-4-yl)-ethyl]-1H-pyrrole-3-carboxylic acid cyclohexylamide The title compound was synthesized in analogy to example 7, using 3-oxo-butyric acid methyl ester as compound of formula R, 2-bromo-1-[2-fluoro-5-(trifluoromethyl)-phenyl]-ethanone as compound of formula S, 4-(2-aminoethyl)-tetrahydropyrane as $R^3$—$(CH_2)_m$—$NH_2$ and 1-cyclohexylamine as $R^1R^2NH$, MS (ISP) 481.6 $(M+H)^+$.

Example 16

(rac) 1-(2,2-Dimethyl-[1,3]dioxolan-4-ylmethyl)-5-(2-fluoro-5-trifluoromethyl-phenyl)-2-methyl-1H-pyrrole-3-carboxylic acid cyclohexylamide The title compound was synthesized in analogy to example 7, using 3-oxo-butyric acid methyl ester as compound of formula R, 2-bromo-1-[2-fluoro-5-(trifluoromethyl)-phenyl]-ethanone as compound of formula S, 2,2-dimethyl-1,3-dioxolan-4-methylamine as $R^3$—$(CH_2)_m$—$NH_2$ and 1-cyclohexylamine as $R^1R^2NH$, MS (ISP) 483.6 $(M+H)^+$.

Example 17

5-(2-Fluoro-5-trifluoromethyl-phenyl)-2-methyl-1-[(S)-1-(tetrahydro-furan-2-yl)methyl]-1H-pyrrole-3-carboxylic acid ((1R,2R)-2-hydroxy-cyclohexyl)-amide The title compound was synthesized in analogy to example 7, using 3-oxo-butyric acid methyl ester as compound of formula R, 2-bromo-1-[2-fluoro-5-(trifluoromethyl)-phenyl]-ethanone as compound of formula S, (S)-tetrahydrofurfurylamine as $R^3$—$(CH_2)_m$—$NH_2$ and (1R,2R)-2-aminocyclohexanol as $R^1R^2NH$, MS (ISP) 469.5 $(M+H)^+$.

Example 18

5-(2-Fluoro-5-trifluoromethyl-phenyl)-2-methyl-1-[(R)-1-(tetrahydro-furan-2-yl)methyl]-1H-pyrrole-3-carboxylic acid cyclohexylamide The title compound was synthesized in analogy to example 7, using 3-oxo-butyric acid methyl ester as compound of formula R, 2-bromo-1-[2-fluoro-5-(trifluoromethyl)-phenyl]-ethanone as compound of formula S, (R)-tetrahydrofurfurylamine as $R^3$—$(CH_2)_m$—$NH_2$ and cyclohexylamine as $R^1R^2NH$, MS (ISP) 453.6 $(M+H)^+$.

Example 19

5-(2-Fluoro-5-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide The title compound was synthesized in analogy to Example 7, using 3-oxo-butyric acid methyl ester as compound of formula R, 2-bromo-1-[2-fluoro-5-(trifluoromethyl)-phenyl]-ethanone as compound of formula S, (R)-tetrahydrofurfurylamine as $R^3$—$(CH_2)_m$—$NH_2$ and (1R,2R)-2-aminocyclohexanol as $R^1R^2NH$, MS (ISP) 469.5 $(M+H)^+$.

Example 20

1-(R)-1-Chroman-2-ylmethyl-5-(2-fluoro-5-trifluoromethyl-phenyl)-2-methyl-1H-pyrrole-3-carboxylic acid cyclohexylamide The title compound was synthesized in analogy to example 7, using 3-oxo-butyric acid methyl ester as compound of formula R, 2-bromo-1-[2-fluoro-5-(trifluoromethyl)-phenyl]-ethanone as compound of formula S, (2R)-3,4-dihydro-2H-1-benzopyran-2-methylamine as $R^3—(CH_2)_m—NH_2$ and cyclohexylamine as $R^1R^2NH$, MS (ISP) 515.5 $(M+H)^+$.

Example 21

2-[5-(5-Chloro-2-fluoro-phenyl)-3-cyclohexylcarbamoyl-2-methyl-pyrrol-1-ylmethyl]-pyrrolidine-1-carboxylic acid tert-butyl ester The title compound was synthesized in analogy to example 7, using 3-oxo-butyric acid methyl ester as compound of formula R, 2-bromo-1-[2-fluoro-5-chlorophenyl]-ethanone as compound of formula S, (R)-2-aminomethyl-pyrrolidine-1-carboxylic acid tert-butyl ester as $R^3—(CH_2)_m—NH_2$ and cyclohexylamine as $R^1R^2NH$, MS (ISP) 518.3 $(M+H)^+$.

Example 22

1-(rac)-(2,2-Dimethyl-[1,3]dioxolan-4-ylmethyl)-5-(2-fluoro-5-trifluoromethyl-phenyl)-2-methyl-1H-pyrrole-3-carboxylic acid ((1R,2R)-2-hydroxy-cyclohexyl)-amide The title compound was synthesized in analogy to example 7, using 3-oxo-butyric acid methyl ester as compound of formula R, 2-bromo-1-[2-fluoro-5-(trifluoromethyl)-phenyl]-ethanone as compound of formula S, 2,2-dimethyl-1,3-dioxolan-4-methylamine as $R^3—(CH_2)_m—NH_2$ and (1R,2R)-2-aminocyclohexanol as $R^1R^2NH$, MS (ISP) 499.5 $(M+H)^+$.

Example 23

5-(2,5-Bis-trifluoromethyl-phenyl)-2-methyl-1-[(R)-1-(tetrahydro-furan-2-yl)methyl]-1H-pyrrole-3-carboxylic acid cyclohexylamide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3—(CH_2)_m—NH_2$ and cyclohexylamine as $R^1R^2NH$, MS (ISP) 503.3 $(M+H)^+$.

Example 24

5-(2,5-Bis-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3—(CH_2)_m—NH_2$ and (1R,2R)-2-aminocyclohexanol as $R^1R^2NH$, MS (ISP) 503.3 $(M+H)^+$.

Example 25

(rac)-5-(2-Chloro-5-trifluoromethyl-phenyl)-1-[1,4]dioxan-2-ylmethyl-2-methyl-1H-pyrrole-3-carboxylic acid cyclohexylamide The title compound was synthesized in analogy to example 7, using 3-oxo-butyric acid methyl ester as compound of formula R, 2-bromo-1-[2-chloro-5-(trifluoromethyl)-phenyl]-ethanone as compound of formula S, 1,4-dioxane-2-methanamine as $R^3—(CH_2)_m—NH_2$ and cyclohexylamine as $R^1R^2NH$, MS (ISP) 485.5 $(M+H)^+$.

Example 26

(rac)-5-(2-Chloro-5-trifluoromethyl-phenyl)-1-(2,2-dimethyl-[1,3]dioxolan-4-ylmethyl)-2-methyl-1H-pyrrole-3-carboxylic acid cyclohexylamide The title compound was synthesized in analogy to example 7, using 3-oxo-butyric acid methyl ester as compound of formula R, 2-bromo-1-[2-chloro-5-(trifluoromethyl)-phenyl]-ethanone as compound of formula S, 2,2-dimethyl-1,3-dioxolan-4-methylamine as $R^3—(CH_2)_m—NH_2$ and 1-cyclohexylamine as $R^1R^2NH$, MS (ISP) 499.4 $(M+H)^+$.

Example 27

5-(2-Chloro-5-trifluoromethyl-phenyl)-1-(rac)-[1,4]dioxan-2-ylmethyl-2-methyl-1H-pyrrole-3-carboxylic acid ((1R,2R)-2-hydroxy-cyclohexyl)-amide The title compound was synthesized in analogy to example 7, using 3-oxo-butyric acid methyl ester as compound of formula R, 2-bromo-1-[2-chloro-5-(trifluoromethyl)-phenyl]-ethanone as compound of formula S, 1,4-dioxane-2-methanamine as $R^3—(CH_2)_m—NH_2$ and (1R,2R)-2-aminocyclohexanol as $R^1R^2NH$, MS (ISP) 501.4 $(M+H)^+$.

Example 28

5-(2-Chloro-5-trifluoromethyl-phenyl)-1-(rac)-(2,2-dimethyl-[1,3]dioxolan-4-ylmethyl)-2-methyl-1H-pyrrole-3-carboxylic acid ((1R,2R)-2-hydroxy-cyclohexyl)-amide The title compound was synthesized in analogy to example 7, using 3-oxo-butyric acid methyl ester as compound of formula R, 2-bromo-1-[2-chloro-5-(trifluoromethyl)-phenyl]-ethanone as compound of formula S, 2,2-dimethyl-1,3-dioxolan-4-methylamine as $R^3—(CH_2)_m—NH_2$ and (1R,2R)-2-aminocyclohexanol as $R^1R^2NH$, MS (ISP) 515.4 $(M+H)^+$.

Example 29

5-(5-Chloro-2-fluoro-phenyl)-2-methyl-1-pyrrolidin-2-ylmethyl-1H-pyrrole-3-carboxylic acid cyclohexylamide; compound with trifluoro-acetic acid Preparation of 5-(5-chloro-2-fluoro-phenyl)-2-methyl-1-pyrrolidin-2-ylmethyl-1H-pyrrole-3-carboxylic acid cyclohexylamide; compound with trifluoro-acetic acid To a solution of 2-[5-(5-chloro-2-fluoro-phenyl)-3-cyclohexylcarbamoyl-2-methyl-pyrrol-1-ylmethyl]-pyrrolidine- 1-carboxylic acid tert-butyl ester (51 mg) in methylene chloride (1 mL) was added at 0° C. TFA (0.5 mL). After 3 hours the volatiles were evacuated in vacuo and the residue was azeotroped with ethyl acetate (3×) and dried on high vacuum overnight to afford the desired title compound (50 mg, 95%) as a pale yellow solid, MS (ISP) 418.1 (M+H)$^+$.

Example 30

(R)-2-[5-(2,5-Bis-trifluoromethyl-phenyl)-3-cyclohexylcarbamoyl-2-methyl-pyrrol-1-ylmethyl]-pyrrolidine-1-carboxylic acid tert-butyl ester The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-2-aminomethyl-pyrrolidine-1-carboxylic acid tert-butyl ester as $R^3$—$(CH_2)_m$—$NH_2$ and cyclohexylamine as $R^1R^2NH$, MS (ISP) 602.3 (M+H)$^+$.

Example 31

(R)-2-[5-(2,5-Bis-trifluoromethyl-phenyl)-3-((1R,2R)-2-hydroxy-cyclohexylcarbamoyl)-2-methyl-pyrrol-1-ylmethyl]-pyrrolidine-1-carboxylic acid tert-butyl ester The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-2-aminomethyl-pyrrolidine-1-carboxylic acid tert-butyl ester as $R^3$—$(CH_2)_m$—$NH_2$ and (1R,2R)-2-aminocyclohexanol as $R^1R^2NH$, MS (ISP) 618.5 (M+H)$^+$.

Example 32

5-(2,5-Bis-trifluoromethyl-phenyl)-2-methyl-1-(R)-1-pyrrolidin-2-ylmethyl-1H-pyrrole-3-carboxylic acid cyclohexylamide; compound with trifluoroacetic acid The title compound was synthesized in analogy to example 29, using (R)-2-[5-(2,5-bis-trifluoromethyl-phenyl)-3-cyclohexylcarbamoyl-2-methyl-pyrrol-1-ylmethyl]-pyrrolidine-1-carboxylic acid tert-butyl ester, MS (ISP) 502.0 (M+H)$^+$.

Example 33

5-(2-Chloro-5-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide The title compound was synthesized in analogy to example 7, using 3-oxo-butyric acid methyl ester as compound of formula R, 2-bromo-1-[2-chloro-5-(trifluoromethyl)-phenyl]-ethanone as compound of formula S, (R)-tetrahydrofurfurylamine as $R^3$—$(CH_2)_m$—$NH_2$ and (1R,2R)-2-aminocyclohexanol as $R^1R^2NH$, MS (ISP) 485.5 (M+H)$^+$.

Example 34

5-(2-Chloro-5-trifluoromethyl-phenyl)-2-methyl-1-[(R)-1-(tetrahydro-furan-2-yl)methyl]-1H-pyrrole-3-carboxylic acid cyclohexylamide The title compound was synthesized in analogy to example 7, using 3-oxo-butyric acid methyl ester as compound of formula R, 2-bromo-1-[2-chloro-5-(trifluoromethyl)-phenyl]-ethanone as compound of formula S, (R)-tetrahydrofurfurylamine as $R^3$—$(CH_2)_m$—$NH_2$ and cyclohexylamine as $R^1R^2NH$, MS (ISP) 469.4 (M+H)$^+$.

Example 35

5-(2,5-Bis-trifluoromethyl-phenyl)-2-methyl-1-[(R)-1-(tetrahydro-furan-2-yl)methyl]-1H-pyrrole-3-carboxylic acid bicyclo[4.1.0]hept-7-ylamide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and bicyclo[3.1.0]hex-6-ylamine as $R^1R^2NH$, MS (ISP) 515.5 (M+H)$^+$.

Example 36

5-(2,5-Bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-methyl-propyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 3-amino-1,1,1-trifluoro-2-methyl-propan-2-ol as $R^1R^2NH$, MS (ISP) 547.3 (M+H)$^+$.

Example 37

5-(3,5-Bis-trifluoromethyl-phenyl)-2-methyl-1-[(R)-1-(tetrahydro-furan-2-yl)methyl]-1H-pyrrole-3-carboxylic acid cyclohexylamide The title compound was synthesized in analogy to example 7, using 3-oxo-butyric acid methyl ester as compound of formula R, 2-bromo-1-[(3,5-bis-trifluoromethyl)phenyl]-ethanone as compound of formula S, (R)-tetrahydrofurfurylamine as $R^3$—$(CH_2)_m$—$NH_2$ and cyclohexylamine as $R^1R^2NH$, MS (ISP) 503.4 (M+H)$^+$.

Example 38

5-(3,5-Bis-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide The title compound was synthesized in analogy to example 7, using 3-oxo-butyric acid methyl ester as compound of formula R, 2-bromo-1-[(3,5-bis-trifluoromethyl)phenyl]-ethanone as compound of formula S, (R)-tetrahydrofurfurylamine as $R^3$—$(CH_2)_m$—$NH_2$ and (1R,2R)-2-aminocyclohexanol as $R^1R^2NH$, MS (ISP) 519.3 (M+H)$^+$.

Example 39

5-(2,5-Bis-trifluoromethyl-phenyl)-2-methyl-1-[(R)-1-(tetrahydro-furan-2-yl)methyl]-1H-pyrrole-3-carboxylic acid (1a,2,3,7b-tetrahydro-1H-cyclopropa[a]naphthalen-1-yl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as R³—(CH₂)ₘ—NH₂ and 1a,2,3,7b-tetrahydro-1H-cyclopropa[a]naphthalen-1-ylamine as R¹R²NH, MS (ISP) 563.5 (M+H)⁺.

Example 40

5-(2,5-Bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-phenyl-propyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as R³—(CH₂)ₘ—NH₂ and 3-amino-1,1,1-trifluoro-2-phenyl-propan-2-ol as R¹R²NH, MS (ISP) 609.2 (M+H)⁺.

Example 41

5-(3,5-Bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-methyl-propyl)-amide The title compound was synthesized in analogy to example 7, using 3-oxo-butyric acid methyl ester as compound of formula R, 2-bromo-1-[(3,5-bis-trifluoromethyl)phenyl]-ethanone as compound of formula S, (R)-tetrahydrofurfurylamine as R³—(CH₂)ₘ—NH₂ and 3-amino-1,1,1-trifluoro-2-methyl-propan-2-ol as R¹R²NH, MS (ISP) 547.3 (M+H)⁺.

Example 42

5-(3,5-Bis-trifluoromethyl-phenyl)-2-methyl-1-[(R)-1-(tetrahydro-furan-2-yl)methyl]-1H-pyrrole-3-carboxylic acid (1S,6R)-bicyclo[4.1.0]hept-7-ylamide The title compound was synthesized in analogy to example 7, using 3-oxo-butyric acid methyl ester as compound of formula R, 2-bromo-1-[(3,5-bis-trifluoromethyl)phenyl]-ethanone as compound of formula S, (R)-tetrahydrofurfurylamine as R³—(CH₂)ₘ—NH₂ and bicyclo[3.1.0]hex-6-ylamine as R¹R²NH, MS (ISP) 515.3 (M+H)⁺.

Example 43 and 44

5-(2,5-Bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-1-methyl-propyl)-amide (diastereoisomeric mixture A) and 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-1-methyl-propyl)-amide (diastereoisomeric mixture B)

The title compounds weres synthesized and obtained as a mixture of two isomers each (mixture A and B) in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as R³—(CH₂)ₘ—NH₂ and 3-amino-1,1,1-trifluoro-butan-2-ol as R¹R²NH. Mixture A: MS (ISP) 547.2 (M+H)⁺; mixture B: MS (ISP) 547.2 (M+H)⁺.

Example 45

(R)-2-[5-(3,5-Bis-trifluoromethyl-phenyl)-3-cyclohexylcarbamoyl-2-methyl-pyrrol-1-ylmethyl]-pyrrolidine-1-carboxylic acid tert-butyl ester The title compound was synthesized in analogy to example 7, using 3-oxo-butyric acid methyl ester as compound of formula R, 2-bromo-1-[(3,5-bis-trifluoromethyl)phenyl]-ethanone as compound of formula S, (R)-2-aminomethyl-pyrrolidine-1-carboxylic acid tert-butyl ester as R³—(CH₂)ₘ—NH₂ and cyclohexylamine as R¹R²NH, MS (ISP) 602.5 (M+H)⁺.

Example 46

(S)-2-[5-(2,5-Bis-trifluoromethyl-phenyl)-3-cyclohexylcarbamoyl-2-methyl-pyrrol-1-ylmethyl]-pyrrolidine-1-carboxylic acid tert-butyl ester The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (S)-2-aminomethyl-pyrrolidine-1-carboxylic acid tert-butyl ester as R³—(CH₂)ₘ—NH₂ and cyclohexylamine as R¹R²NH, MS (ISP) 602.3 (M+H)⁺.

Example 47

5-(2,5-Bis-trifluoromethyl-phenyl)-2-methyl-1-[(R)-1-(tetrahydro-furan-2-yl)methyl]-1H-pyrrole-3-carboxylic acid (2-methoxy-1-methyl-2-phenyl-ethyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as R³—(CH₂)ₘ—NH₂ and 3-methoxy-4,7,7-trimethyl-bicyclo[2.2.1]hept-2-ylamine as R¹R²NH, MS (ISP) 587.3 (M+H)⁺.

Example 48

5-(2,5-Bis-trifluoromethyl-phenyl)-2-methyl-1-[(R)-1-(tetrahydro-furan-2-yl)methyl]-1H-pyrrole-3-carboxylic acid (3-methoxy-4,7,7-trimethyl-bicyclo[2.2.1]hept-2-yl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as R³—(CH₂)ₘ—NH₂ and 3-methoxy-4,7,7-trimethyl-bicyclo[2.2.1]hept-2-ylamine as R¹R²NH, MS (ISP) 587.3 (M+H)⁺.

Example 49

Acetic acid 3-({5-(2,5-bis-trifluoromethyl-phenyl)-2-methyl-1-[(R)-1-(tetrahydro-furan-2-yl)methyl]-1H-pyrrole-3-carbonyl}-amino)-1,7,7-trimethyl-bicyclo[2.2.1]hept-2-yl ester The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_n$—$NH_2$ and acetic acid 3-amino-1,7,7-trimethyl-bicyclo[2.2.1]hept-2-yl ester as $R^1R^2NH$, MS (ISP) 615.5 (M+H)$^+$.

Example 50

5-(2,5-Bis-trifluoromethyl-phenyl)-2-methyl-1-[(R)-1-(tetrahydro-furan-2-yl)methyl]-1H-pyrrole-3-carboxylic acid (2-hydroxy-2-methyl-propyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 1-amino-2-methyl-propan-2-ol as $R^1R^2NH$, MS (ISP) 493.4 (M+H)$^+$.

Example 51

5-(2,5-Bis-trifluoromethyl-phenyl)-2-methyl-1-[(R)-1-(tetrahydro-furan-2-yl)methyl]-1H-pyrrole-3-carboxylic acid (2-hydroxy-2-phenyl-propyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 1-amino-2-phenyl-propan-2-ol as $R^1R^2NH$, MS (ISP) 555.3 (M+H)$^+$.

Example 52

5-(2,5-Bis-trifluoromethyl-phenyl)-2-methyl-1-[(R)-1-(tetrahydro-furan-2-yl)methyl]-1H-pyrrole-3-carboxylic acid (2-hydroxy-3-methoxy-propyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 1-amino-3-methoxy-propan-2-ol as $R^1R^2NH$, MS (ISP) 509.4 (M+H)$^+$.

Example 53

5-(2,5-Bis-trifluoromethyl-phenyl)-2-methyl-1-[(R)-1-(tetrahydro-furan-2-yl)methyl]-1H-pyrrole-3-carboxylic acid (2-methoxy-2-phenyl-ethyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 2-methoxy-2-phenyl-ethylamine as $R^1R^2NH$, MS (ISP) 555.3 (M+H)$^+$.

Example 54

5-(2,5-Bis-trifluoromethyl-phenyl)-2-methyl-1-[(R)-1-(tetrahydro-furan-2-yl)methyl]-1H-pyrrole-3-carboxylic acid (2-hydroxy-2-phenyl-ethyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 2-amino-1-phenyl-ethanol as $R^1R^2NH$, MS (ISP) 541.2 (M+H)$^+$.

Example 55

5-(2,5-Bis-trifluoromethyl-phenyl)-2-methyl-1-[(R)-1-(tetrahydro-furan-2-yl)methyl]-1H-pyrrole-3-carboxylic acid (2-hydroxy-3-morpholin-4-yl-propyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 1-amino-3-morpholin-4-yl-propan-2-ol as $R^1R^2NH$, MS (ISP) 564.3 (M+H)$^+$.

Example 56

5-(3,5-Bis-trifluoromethyl-phenyl)-2-methyl-1-(R)-1-pyrrolidin-2-ylmethyl-1H-pyrrole-3-carboxylic acid cyclohexylamide The title compound was synthesized in analogy to example 29, using (R)-2-[5-(3,5-bis-trifluoromethyl-phenyl)-3-cyclohexylcarbamoyl-2-methyl-pyrrol-1-ylmethyl]-pyrrolidine-1-carboxylic acid tert-butyl ester, MS (ISP) 502.2 (M+H)$^+$.

Example 57

5-(2,5-Bis-trifluoromethyl-phenyl)-2-methyl-1-(S)-1-pyrrolidin-2-ylmethyl-1H-pyrrole-3-carboxylic acid cyclohexylamide The title compound was synthesized in analogy to example 29, using (S)-2-[5-(2,5-bis-trifluoromethyl-phenyl)-3-cyclohexylcarbamoyl-2-methyl-pyrrol-1-ylmethyl]-pyrrolidine-1-carboxylic acid tert-butyl ester, MS (ISP) 502.3 (M+H)$^+$.

Example 58

5-(2,5-Bis-trifluoromethyl-phenyl)-2-methyl-1-[(R)-1-(tetrahydro-furan-2-yl)methyl]-1H-pyrrole-3-carboxylic acid (3-hydroxy-4,7,7-trimethyl-bicyclo[2.2.1]hept-2-yl)-amide To a solution of acetic acid 3-({5-(2,5-bis-trifluoromethyl-phenyl)-2-methyl-1-[(R)-1-(tetrahydro-furan-2-yl)methyl]-1H-pyrrole-3-carbonyl}-amino)-1,7,7-trimethyl-bicyclo[2.2.1]hept-2-yl ester (60 mg) in MeOH (2 mL) was added 15 μL of a 1N $K_2CO_3$ solution. After 18 hours the reaction mixture was extracted with ethyl acetate and the organic phases were washed with brine, dried over sodium sulfate and filtered. Removal of the volatiles in vacuo and chromatography of the crude residue afforded the title compound (54 mg), MS (ISP) 631.5 (M+H)$^+$.

Example 59

5-(2-Chloro-5-trifluoromethyl-phenyl)-2-methyl-1-((S)-2-methyl-tetrahydro-furan-2-ylmethyl)-1H-pyrrole-3-carboxylic acid ((1R,2R)-2-hydroxy-cyclohexyl)-amide Isomer I The title compound was synthesized in analogy to example 7, using 3-oxo-butyric acid methyl ester as compound of formula R, 2-bromo-1-[2-chloro-5-(trifluoromethyl)-phenyl]-ethanone as compound of formula S, tetrahydro-2-methyl-2-furanmethanamine as $R^3$—$(CH_2)_m$—$NH_2$ and (1R, 2R)-2-aminocyclohexanol as $R^1R^2NH$. Enantiomers of the 5-(2-chloro-5-trifluoromethyl-phenyl)-2-methyl-1-(−2-methyl-tetrahydro-furan-2-ylmethyl)-1H-pyrrole-3-carboxylic acid methyl ester were separated on ChiralPak AD (2% isopropanol/heptane) and the (−)-enantiomer was processed to Isomer I; MS (ISP) 499.4 (M+H)$^+$.

Example 60

5-(2-Chloro-5-trifluoromethyl-phenyl)-2-methyl-1-((R)-2-methyl-tetrahydro-furan-2-ylmethyl)-1H-pyrrole-3-carboxylic acid ((1R,2R)-2-hydroxy-cyclohexyl)-amide Isomer II The title compound was synthesized in analogy to example 7, using 3-oxo-butyric acid methyl ester as compound of formula R, 2-bromo-1-[2-chloro-5-(trifluoromethyl)-phenyl]-ethanone as compound of formula S, tetrahydro-2-methyl-2-furanmethanamine as $R^3$—$(CH_2)_m$—$NH_2$ and (1R, 2R)-2-aminocyclohexanol as $R^1R^2NH$. Enantiomers of the 5-(2-chloro-5-trifluoromethyl-phenyl)-2-methyl-1-(−2-methyl-tetrahydro-furan-2-ylmethyl)-1H-pyrrole-3-carboxylic acid methyl ester were separated on ChiralPak AD (2% isopropanol/heptane) and the (+)-enantiomer was processed to Isomer II; MS (ISP) 499.4 (M+H)$^+$.

Example 61

5-(2-Chloro-5-trifluoromethyl-phenyl)-2-methoxymethyl-1-[(R)-1-(tetrahydro-furan-2-yl)methyl]-1H-pyrrole-3-carboxylic acid cyclohexylamide The title compound was synthesized in analogy to example 7, using 4-methoxy-3-oxo-butanoic acid methyl ester as compound of formula R, 2-bromo-1-[2-chloro-5-(trifluoromethyl)phenyl]-ethanone as compound of formula S, (R)-tetrahydro-furfurylamine as $R^3$—$(CH_2)_m$—$NH_2$ and cyclohexylamine as $R^1R^2NH$, MS (ISP) 499.4 (M+H)$^+$.

Example 62

5-(2,5-Bis-trifluoromethyl-phenyl)-2-methyl-1-[(R)-1-(tetrahydro-furan-2-yl)methyl]-1H-pyrrole-3-carboxylic acid ((R)-2-hydroxy-2-phenyl-ethyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and (R)-2-amino-1-phenyl-ethanol as $R^1R^2NH$, MS (ISP) 541.2 (M+H)$^+$.

Example 63

5-(2,5-Bis-trifluoromethyl-phenyl)-1-[1,4]dioxan-2-ylmethyl-2-methyl-1H-pyrrole-3-carboxylic acid ((1R,2R)-2-hydroxy-cyclohexyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, 1,4-dioxane-2-methanamine as $R^3$—$(CH_2)_m$—$NH_2$ and (1R,2R)-2-aminocyclohexanol as $R^1R^2NH$, MS (ISP) 535.5 (M+H)$^+$.

Example 64

5-(2,5-Bis-trifluoromethyl-phenyl)-1-[1,4]dioxan-2-ylmethyl-2-methyl-1H-pyrrole-3-carboxylic acid (2-hydroxy-2-phenyl-propyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, 1,4-dioxane-2-methanamine as $R^3$—$(CH_2)_m$—$NH_2$ and 1-amino-2-phenyl-propan-2-ol as $R^1R^2NH$, MS (ISP) 571.3 (M+H)$^+$.

Example 65

5-(2,5-Bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-ethyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 2-amino-1-cyclopropyl-ethanol as $R^1R^2NH$, MS (ISP) 505.1 (M+H)$^+$.

Example 66

5-(2,5-Bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-propyl)-amide The title compound was synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 1-amino-2-cyclopropyl-propan-2-ol as $R^1R^2NH$, MS (ISP) 519.3 (M+H)$^+$.

Example 67

5-(3,5-Bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-propyl)-amide The title compound was synthesized in analogy to example 7, using 3-oxo-butyric acid methyl ester as compound of formula R, 2-bromo-1-[(3,5-bis-trifluoromethyl)phenyl]-ethanone as compound of formula S, (R)-tetrahydrofurfurylamine as $R^3$—$(CH_2)_m$—$NH_2$ and 1-amino-2-cyclopropyl-propan-2-ol as $R^1R^2NH$, MS (ISP) 519.3 (M+H)$^+$.

Example 68 and 69

5-(3,5-Bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-propyl)-amide (diastereomeric mixture A) and 5-(3,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide (diastereomeric mixture B)

The title compounds were synthesized in analogy to example 7, using 3-oxo-butyric acid methyl ester as compound of formula R, 2-bromo-1-[(3,5-bis-trifluoromethyl)phenyl]-ethanone as compound of formula S, (R)-tetrahydrofurfurylamine as $R^3$—$(CH_2)_m$—$NH_2$ and 2-amino-1-cyclopropyl-propan-1-ol as $R^1R^2NH$, MS (mixture A) (ISP) 519.3 $(M+H)^+$, MS (mixture B) (ISP) 535.5 $(M+NH_4)^+$ Example 70 and 71

5-(2,5-Bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide (diastereomeric mixture A) and 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide (diastereomeric mixture B)

The title compounds were synthesized in analogy to example 7, using 3-oxo-butyric acid methyl ester as compound of formula R, 2-bromo-1-[(2,5-bis-trifluoromethyl)phenyl]-ethanone as compound of formula S, (R)-tetrahydrofurfurylamine as $R^3$—$(CH_2)_m$—$NH_2$ and 2-amino-1-cyclopropyl-propan-1-ol as $R^1R^2NH$, MS (mixture A) (ISP) 519.3 $(M+H)^+$, MS (mixture B) (ISP) 535.5 $(M+NH_4)^+$.

GALENICAL EXAMPLES

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |

| Ingredients | Per capsule |
|---|---|
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

What is claimed is:
1. A compound of the formula

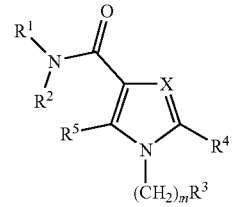

wherein
X is C—$R^6$;
$R^1$ is hydrogen or lower alkyl;
$R^2$ is selected from the group consisting of lower alkyl which is unsubstituted or substituted by one, two or three groups independently selected from the group consisting of hydroxy, lower alkoxy, fluorinated lower alkyl, fluorinated lower alkoxy, phenyl, cycloalkyl and a 5- or 6-membered saturated heterocyclic ring containing one or two heteroatoms independently selected from nitrogen and oxygen;
fluorinated lower alkyl;
cycloalkyl which is unsubstituted or substituted by one, two, three or four groups independently selected from the group consisting of hydroxy, lower alkyl, lower alkoxy, fluorinated lower alkyl and fluorinated lower alkoxy;
a 5- or 6-membered saturated heterocyclic ring containing one or two heteroatoms independently selected from nitrogen and oxygen, said heterocyclic ring being unsubstituted or substituted by one, two or three groups independently selected from the group consisting of hydroxy, lower alkyl, lower alkoxy, amino, lower alkylamino, oxo, fluorinated lower alkyl and fluorinated lower alkoxy;
bicyclo[4.1.0]hept-7-yl which is unsubstituted or substituted by one, two or three groups independently selected from the group consisting of lower alkyl, hydroxy and lower alkoxy, or is condensed with a phenyl ring;

and 4,7,7-trimethylbicyclo[2.2.1]hept-2-yl which is unsubstituted or substituted by one, two or three groups independently selected from the group consisting of hydroxy, lower alkoxy and lower acyloxy;

$R^3$ is a 5- or 6-membered saturated heterocyclic ring containing one or two oxygen atoms, said heterocyclic ring being unsubstituted or substituted by one, two or three lower alkyl groups, or being condensed with a phenyl ring or $R^3$ is a pyrrolidine ring being unsubstituted or substituted by lower alkyl or alkoxycarbonyl;

$R^4$ is phenyl, unsubstituted or substituted by one, two or three groups independently selected from the group consisting of hydroxy, lower alkyl, lower alkoxy, halogen, halogenated lower alkyl and halogenated lower alkoxy;

$R^5$ is selected from the group consisting of hydrogen, lower alkyl and lower alkoxyalkyl;

$R^6$ is hydrogen or lower alkyl;

m is 1 or 2;

and pharmaceutically acceptable salts thereof.

2. The compound of claim 1, wherein $R^1$ is hydrogen.

3. The compound of claim 1, wherein $R^2$ is lower alkyl, unsubstituted or substituted by one, two or three groups independently selected from the group consisting of hydroxy, lower alkoxy, fluorinated lower alkyl, fluorinated lower alkoxy, phenyl, cycloalkyl and a 5- or 6-membered saturated heterocyclic ring containing one or two heteroatoms independently selected from nitrogen and oxygen.

4. The compound of claim 1, wherein $R^2$ is fluorinated lower alkyl.

5. The compound of claim 1, wherein $R^2$ is a cycloalkyl group with three to seven carbon atoms which is unsubstituted or substituted by one, two or three groups independently selected from lower alkyl or hydroxy.

6. The compound of claim 1, wherein $R^2$ is a 5- or 6-membered saturated heterocyclic ring containing one or two heteroatoms independently selected from nitrogen and oxygen, said heterocyclic ring being unsubstituted or being substituted by one, two or three groups independently selected from the group consisting of hydroxy, lower alkyl, lower alkoxy, amino, lower alkylamino, oxo, fluorinated lower alkyl and fluorinated lower alkoxy.

7. The compound of claim 1, wherein $R^2$ is bicyclo[4.1.0]hept-7-yl which is unsubstituted or substituted by one, two or three groups independently selected from the group consisting of lower alkyl, hydroxy and lower alkoxy, or is condensed with a phenyl ring; or 4,7,7-trimethylbicyclo[2.2.1]hept-2-yl which is unsubstituted or substituted by hydroxy, lower alkoxy or lower acyloxy.

8. The compound of claim 1, wherein $R^3$ is selected from the group consisting of tetrahydropyranyl, tetrahydrofuranyl, 2-methyl-tetrahydrofuranyl, 2,2-dimethyl-[1,3]-dioxolan-4-yl, [1,4]-dioxan-2-yl and 1-chroman-2-yl.

9. The compound of claim 1, wherein $R^4$ is phenyl substituted by one, two or three groups independently selected from the group consisting of hydroxy, lower alkyl, lower alkoxy, halogen, halogenated lower alkyl and halogenated lower alkoxy.

10. The compound of claim 1, wherein $R^5$ is lower alkyl.

11. The compound of claim 10, wherein $R^5$ is methyl.

12. The compound of claim 1, wherein X is C—$R^6$ and $R^6$ is hydrogen.

13. The compound of claim 1, wherein m is 1.

14. The compound of claim 1, selected from the group consisting of:

5-(5-chloro-2-methoxy-4-methyl-phenyl)-1-[1,4]dioxan-2-ylmethyl-2-methyl-1H-pyrrole-3-carboxylic acid piperidin-1-ylamide, 2-methyl-1-[(S)-1-(tetrahydro-furan-2-yl)methyl]-5-(2-trifluoromethoxy-phenyl)-1H-pyrrole-3-carboxylic acid cyclohexylamide, 2-methyl-1-[(R)-1-(tetrahydro-furan-2-yl)methyl]-5-(2-trifluoromethoxy-phenyl)-1H-pyrrole-3-carboxylic acid cyclohexylamide, (rac)-1-(2,2-dimethyl-[1,3]dioxolan-4-ylmethyl)-2-methyl-5-(2-trifluoromethoxy-phenyl)-1H-pyrrole-3-carboxylic acid cyclohexylamide, and (rac)-1-[1,4]dioxan-2-ylmethyl-2-methyl-5-(2-trifluoromethoxy-phenyl)-1H-pyrrole-3-carboxylic acid cyclohexylamide.

15. The compound of claim 1, selected from the group consisting of:

2-methyl-1-[(R)-1-(tetrahydro-furan-2-yl)methyl]-5-(2-trifluoromethoxy-phenyl)-1H-pyrrole-3-carboxylic acid ((1RS,2RS)-2-hydroxy-cyclohexyl)-amide, 5-(2-fluoro-5-trifluoromethyl-phenyl)-2-methyl-1-[2-(tetrahydro-pyran-4-yl)-ethyl]-1H-pyrrole-3-carboxylic acid cyclohexylamide, (rac)-1-(2,2-dimethyl-[1,3]dioxolan-4-ylmethyl)-5-(2-fluoro-5-trifluoromethyl-phenyl)-2-methyl-1H-pyrrole-3-carboxylic acid cyclohexylamide, 5-(2-fluoro-5-trifluoromethyl-phenyl)-2-methyl-1-[(S)-1-(tetrahydro-furan-2-yl)methyl]-1H-pyrrole-3-carboxylic acid ((1R,2R)-2-hydroxy-cyclohexyl)-amide, 5-(2-fluoro-5-trifluoromethyl-phenyl)-2-methyl-1-[(R)-1-(tetrahydro-furan-2-yl)methyl]-1H-pyrrole-3-carboxylic acid cyclohexylamide, 5-(2-fluoro-5-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, and 1-(R)-1-chroman-2-ylmethyl-5-(2-fluoro-5-trifluoromethyl-phenyl)-2-methyl-1H-pyrrole-3-carboxylic acid cyclohexylamide.

16. The compound of claim 1, selected from the group consisting of:

2-[5-(5-chloro-2-fluoro-phenyl)-3-cyclohexylcarbamoyl-2-methyl-pyrrol-1-ylmethyl]-pyrrolidine-1-carboxylic acid tert-butyl ester, 1-(rac)-(2,2-dimethyl-[1,3]dioxolan-4-ylmethyl)-5-(2-fluoro-5-trifluoromethyl-phenyl)-2-methyl-1H-pyrrole-3-carboxylic acid ((1R,2R)-2-hydroxy-cyclohexyl)-amide, 5-(2,5-bis-trifluoromethyl-phenyl)-2-methyl-1-[(R)-1-(tetrahydro-furan-2-yl)methyl]-1H-pyrrole-3-carboxylic acid cyclohexylamide, 5-(2,5-bis-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, (rac)-5-(2-chloro-5-trifluoromethyl-phenyl)-1-[1,4]dioxan-2-ylmethyl-2-methyl-1H-pyrrole-3-carboxylic acid cyclohexylamide, (rac)-5-(2-chloro-5-trifluoromethyl-phenyl)-1-(2,2-dimethyl-[1,3]dioxolan-4-ylmethyl)-2-methyl-1H-pyrrole-3-carboxylic acid cyclohexylamide, 5-(2-chloro-5-trifluoromethyl-phenyl)-1-(rac)-[1,4]dioxan-2-ylmethyl-2-methyl-1H-pyrrole-3-carboxylic acid ((1R,2R)-2-hydroxy-cyclohexyl)-amide, 5-(2-chloro-5-trifluoromethyl-phenyl)-1-(rac)-(2,2-dimethyl-[1,3]dioxolan-4-ylmethyl)-2-methyl-1H-pyrrole-3-carboxylic acid ((1R,2R)-2-hydroxy-cyclohexyl)-amide, 5-(5-chloro-2-fluoro-phenyl)-2-methyl-1-pyrrolidin-2-ylmethyl-1Hl-pyrrole-3-carboxylic acid cyclohexylamide; compound with trifluoro-acetic acid, and (R)-2-[5-(2,5-bis-trifluoromethyl-phenyl)-3-cyclohexyl-carbamoyl-2-methyl-pyrrol-1-ylmethyl]-pyrrolidine-1-carboxylic acid tert-butyl ester.

17. The compound of claim 1, selected from the group consisting of:
- (R)-2-[5-(2,5-bis-trifluoromethyl-phenyl)-3-((1R,2R)-2-hydroxy-cyclohexylcarbamoyl)-2-methyl-pyrrol-1-ylmethyl]-pyrrolidine-1-carboxylic acid tert-butyl ester,
- 5-(2,5-bis-trifluoromethyl-phenyl)-2-methyl-1-(R)-1-pyrrolidin-2-ylmethyl-1H-pyrrole-3-carboxylic acid cyclohexylamide; compound with trifluoro-acetic acid,
- 5-(2-chloro-5-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide,
- 5-(2-chloro-5-trifluoromethyl-phenyl)-2-methyl-1-[(R)-1-(tetrahydro-furan-2-yl)methyl]-1H-pyrrole-3-carboxylic acid cyclohexylamide,
- 5-(2,5-bis-trifluoromethyl-phenyl)-2-methyl-1-[(R)-1-(tetrahydro-furan-2-yl)methyl]-1H-pyrrole-3-carboxylic acid bicyclo[4.1.0]hept-7-ylamide,
- 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-methyl-propyl)-amide,
- 5-(3,5-bis-trifluoromethyl-phenyl)-2-methyl-1-[(R)-1-(tetrahydro-furan-2-yl)methyl]-1H-pyrrole-3-carboxylic acid cyclohexylamide,
- 5-(3,5-bis-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide,
- 5-(2,5-bis-trifluoromethyl-phenyl)-2-methyl-1-[(R)-1-(tetrahydro-furan-2-yl)methyl]-1H-pyrrole-3-carboxylic acid (1a,2,3,7b-tetrahydro-1H-cyclopropa[a]naphthalen-1-yl)-amide, and
- 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-phenyl-propyl)-amide.

18. The compound of claim 1, selected from the group consisting of:
- 5-(3,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-methyl-propyl)-amide,
- 5-(3,5-bis-trifluoromethyl-phenyl)-2-methyl-1-[(R)-1-(tetrahydro-furan-2-yl)methyl]-1H-pyrrole-3-carboxylic acid (1S,6R)-bicyclo[4.1.0]hept-7-ylamide,
- 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-1-methyl-propyl)-amide,
- 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-1-methyl-propyl)-amide,
- (R)-2-[5-(3,5-bis-trifluoromethyl-phenyl)-3-cyclohexyl-carbamoyl-2-methyl-pyrrol-1-ylmethyl]-pyrrolidine-1-carboxylic acid tert-butyl ester,
- (S)-2-[5-(2,5-bis-trifluoromethyl-phenyl)-3-cyclohexyl-carbamoyl-2-methyl-pyrrol-1-ylmethyl]-pyrrolidine-1-carboxylic acid tert-butyl ester,
- 5-(2,5-bis-trifluoromethyl-phenyl)-2-methyl-1-[(R)-1-(tetrahydro-furan-2-yl)methyl]-1H-pyrrole-3-carboxylic acid (2-methoxy-1-methyl-2-phenyl-ethyl)-amide,
- 5-(2,5-bis-trifluoromethyl-phenyl)-2-methyl-1-[(R)-1-(tetrahydro-furan-2-yl)methyl]-1H-pyrrole-3-carboxylic acid (3-methoxy-4,7,7-trimethyl-bicyclo[2.2.1]hept-2-yl)-amide,
- acetic acid 3-({5-(2,5-bis-trifluoromethyl-phenyl)-2-methyl-1-[(R)-1-(tetrahydro-furan-2-yl)methyl]-1H-pyrrole-3-carbonyl}-amino)-1,7,7-trimethyl-bicyclo[2.2.1]hept-2-yl ester, and
- 5-(2,5-bis-trifluoromethyl-phenyl)-2-methyl-1-[(R)-1-(tetrahydro-furan-2-yl)methyl]-1H-pyrrole-3-carboxylic acid (2-hydroxy-2-methyl-propyl)-amide.

19. The compound of claim 1, selected from the group consisting of:
- 5-(2,5-bis-trifluoromethyl-phenyl)-2-methyl-1-[(R)-1-(tetrahydro-furan-2-yl)methyl]-1H-pyrrole-3-carboxylic acid (2-hydroxy-2-phenyl-propyl)-amide,
- 5-(2,5-bis-trifluoromethyl-phenyl)-2-methyl-1-[(R)-1-(tetrahydro-furan-2-yl)methyl]-1H-pyrrole-3-carboxylic acid (2-hydroxy-3-methoxy-propyl)-amide,
- 5-(2,5-bis-trifluoromethyl-phenyl)-2-methyl-1-[(R)-1-(tetrahydro-furan-2-yl)methyl]-1H-pyrrole-3-carboxylic acid (2-methoxy-2-phenyl-ethyl)-amide,
- 5-(2,5-bis-trifluoromethyl-phenyl)-2-methyl-1-[(R)-1-(tetrahydro-furan-2-yl)methyl]-1H-pyrrole-3-carboxylic acid (2-hydroxy-2-phenyl-ethyl)-amide,
- 5-(2,5-bis-trifluoromethyl-phenyl)-2-methyl-1-[(R)-1-(tetrahydro-furan-2-yl)methyl]-1H-pyrrole-3-carboxylic acid (2-hydroxy-3-morpholin-4-yl-propyl)-amide,
- 5-(3,5-bis-trifluoromethyl-phenyl)-2-methyl-1-(R)-1-pyrrolidin-2-ylmethyl-1H-pyrrole-3-carboxylic acid cyclohexylamide,
- 5-(2,5-bis-trifluoromethyl-phenyl)-2-methyl-1-(S)-1-pyrrolidin-2-ylmethyl-1H-pyrrole-3-carboxylic acid cyclohexylamide,
- 5-(2,5-bis-trifluoromethyl-phenyl)-2-methyl-1-[(R)-1-(tetrahydro-furan-2-yl)methyl]-1H-pyrrole-3-carboxylic acid (3-hydroxy-4,7,7-trimethyl-bicyclo[2.2.1]hept-2-yl)-amide,
- 5-(2-chloro-5-trifluoromethyl-phenyl)-2-methyl-1-((S)-2-methyl-tetrahydro-furan-2-ylmethyl)-1H-pyrrole-3-carboxylic acid ((1R,2R)-2-hydroxy-cyclohexyl)-amide, and
- 5-(2-chloro-5-trifluoromethyl-phenyl)-2-methyl-1-((R)-2-methyl-tetrahydro-furan-2-ylmethyl)-1H-pyrrole-3-carboxylic acid ((1R,2R)-2-hydroxy-cyclohexyl)-amide.

20. The compound of claim 1, selected from the group consisting of:
- 5-(2-chloro-5-trifluoromethyl-phenyl)-2-methoxymethyl-1-[(R)-1-(tetrahydro-furan-2-yl)methyl]-1H-pyrrole-3-carboxylic acid cyclohexylamide,
- 5-(2,5-bis-trifluoromethyl-phenyl)-2-methyl-1-[(R)-1-(tetrahydro-furan-2-yl)methyl]-1H-pyrrole-3-carboxylic acid ((S)-2-hydroxy-2-phenyl-ethyl)-amide,
- 5-(2,5-bis-trifluoromethyl-phenyl)-1-[1,4]dioxan-2-ylmethyl-2-methyl-1H-pyrrole-3-carboxylic acid ((1R,2R)-2-hydroxy-cyclohexyl)-amide,
- 5-(2,5-bis-trifluoromethyl-phenyl)-1-[1,4]dioxan-2-ylmethyl-2-methyl-1H-pyrrole-3-carboxylic acid (2-hydroxy-2-phenyl-propyl)-amide,
- 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-ethyl)-amide,
- 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-propyl)-amide, 5-(3,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-propyl)-amide, 5-(3,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide, 5-(3,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide, 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide, and 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-1-methyl-ethyl)-amide.

21. The compound of claim 1, selected from the group consisting of:

5-(2-fluoro-5-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, 5-(3,5-bis-trifluoromethyl-phenyl)-2-methyl-1-[(R)-1-(tetrahydro-furan-2-yl)methyl]-1H-pyrrole-3-carboxylic acid ((1R,2R)-2-hydroxy-cyclohexyl)-amide, 5-(2,5-bis-trifluoromethyl-phenyl)-2-methyl-1-[(R)-1-(tetrahydro-furan-2-yl)methyl]-1H-pyrrole-3-carboxylic acid (1a,2,3,7b-tetrahydro-1H-cyclopropa[a]naphthalen-1-yl)-amide, 5-(2,5-bis-trifluoromethyl-phenyl)-2-methyl-1-[(R)-1-(tetrahydro-furan-2-yl)methyl]-1H-pyrrole-3-carboxylic acid (3,3,3-trifluoro-2-hydroxy-2-phenyl-propyl)-amide, 5-(2,5-bis-trifluoromethyl-phenyl) 1-[1,4]dioxan-2-ylmethyl-2-methyl-1H-pyrrole-3-carboxylic acid ((1R,2R)-2-hydroxy-cyclohexyl)-amide, 5-(2,5-bis-trifluoromethyl-phenyl)-1-[1,4]dioxan-2-ylmethyl-2-methyl-1H-pyrrole-3-carboxylic acid (2-hydroxy-2-phenyl-propyl)-amide, and 5-(2,5-bis-trifluoromethyl-phenyl)-2-methyl-1-[(R)-1-(tetrahydro-furan-2-yl)methyl]-1H-pyrrole-3-carboxylic acid (2-cyclopropyl-2-hydroxy-propyl)-amide, and pharmaceutically acceptable salts thereof.

22. A pharmaceutical composition comprising a pharmacologically effective amount of a compound of claim 1 and a pharmaceutically acceptable carrier and/or adjuvant.

* * * * *